(12) United States Patent
Agrafiotis et al.

(10) Patent No.: US 7,054,757 B2
(45) Date of Patent: May 30, 2006

(54) METHOD, SYSTEM, AND COMPUTER PROGRAM PRODUCT FOR ANALYZING COMBINATORIAL LIBRARIES

(75) Inventors: Dimitris K Agrafiotis, Downingtown, PA (US); Victor S Lobanov, Yardley, PA (US); Francis R Salemme, Yardley, PA (US)

(73) Assignee: Johnson & Johnson Pharmaceutical Research & Development, L.L.C., Raritan, NJ (US)

( * ) Notice: Subject to any disclaimer, the term of this patent is extended or adjusted under 35 U.S.C. 154(b) by 86 days.

(21) Appl. No.: 10/058,216

(22) Filed: Jan. 29, 2002

(65) Prior Publication Data

US 2002/0143476 A1    Oct. 3, 2002

Related U.S. Application Data

(63) Continuation-in-part of application No. 09/934,084, filed on Aug. 22, 2001, now Pat. No. 6,834,239.

(60) Provisional application No. 60/264,258, filed on Jan. 29, 2001, provisional application No. 60/274,238, filed on Mar. 9, 2001.

(51) Int. Cl.
*G01N 33/48* (2006.01)
*G06F 7/00* (2006.01)
*C12Q 1/68* (2006.01)

(52) U.S. Cl. .......................... 702/19; 702/20; 702/22; 702/27; 702/30; 707/102; 703/11; 435/6; 435/DIG. 51

(58) Field of Classification Search ................ 702/19, 702/22
See application file for complete search history.

(56) References Cited

U.S. PATENT DOCUMENTS

| | | | |
|---|---|---|---|
| 4,773,099 A | 9/1988 | Bokser | 382/14 |
| 4,811,217 A | 3/1989 | Tokizane et al. | 364/300 |
| 4,859,736 A | 8/1989 | Rink | 525/54.1 |
| 4,908,773 A | 3/1990 | Pantoliano et al. | 364/496 |
| 4,935,875 A | 6/1990 | Shah et al. | 364/497 |
| 4,939,666 A | 7/1990 | Hardman | 364/496 |
| 5,010,175 A | 4/1991 | Rutter et al. | 530/334 |
| 5,025,388 A | 6/1991 | Cramer, III et al. | 364/496 |
| 5,095,443 A | 3/1992 | Watanabe | 364/513 |
| 5,155,801 A | 10/1992 | Lincoln | 395/22 |
| 5,167,009 A | 11/1992 | Skeirik | 395/22 |
| 5,181,259 A | 1/1993 | Rorvig | 395/27 |
| 5,240,680 A | 8/1993 | Zuckermann et al. | 382/36 |
| 5,260,882 A | 11/1993 | Blanco et al. | 422/67 |
| 5,265,030 A | 11/1993 | Skolnick et al. | 364/494 |
| 5,270,170 A | 12/1993 | Schatz et al. | 364/496 |
| 5,288,514 A | 2/1994 | Ellman | 435/7.37 |
| 5,307,287 A | 4/1994 | Cramer, III et al. | 427/2 |
| 5,323,471 A | 6/1994 | Hayashi | 364/496 |
| 5,331,573 A | 7/1994 | Balaji et al. | 382/15 |
| 5,434,796 A | 7/1995 | Weininger | 364/500 |
| 5,436,850 A | 7/1995 | Eisenberg et al. | 364/496 |
| 5,442,122 A | 8/1995 | Noda et al. | 564/426 |
| 5,463,564 A | 10/1995 | Agrafiotis et al. | 364/496 |
| 5,499,193 A | 3/1996 | Sugawara et al. | 364/500 |
| 5,519,635 A | 5/1996 | Miyake et al. | 364/497 |
| 5,524,065 A | 6/1996 | Yagasaki | 382/226 |
| 5,526,281 A | 6/1996 | Chapman et al. | 364/496 |
| 5,545,568 A | 8/1996 | Ellman | 436/518 |
| 5,549,974 A | 8/1996 | Holmes | 428/403 |
| 5,553,225 A | 9/1996 | Perry | 395/157 |
| 5,565,325 A | 10/1996 | Blake | 435/7.1 |
| 5,574,656 A | 11/1996 | Agrafiotis et al. | 364/500 |
| 5,585,277 A | 12/1996 | Bowie et al. | 436/518 |
| 5,598,510 A | 1/1997 | Castelaz | 395/23 |
| 5,602,755 A | 2/1997 | Ashe et al. | 364/498 |
| 5,602,938 A | 2/1997 | Akiyama et al. | 382/155 |
| 5,612,895 A | 3/1997 | Balaji et al. | 364/496 |
| 5,621,861 A | 4/1997 | Hayashi et al. | 395/23 |
| 5,634,017 A | 5/1997 | Mohanty et al. | 395/326 |
| 5,635,598 A | 6/1997 | Lebl et al. | 530/334 |
| 5,670,326 A | 9/1997 | Beutel | 435/7.1 |
| 5,679,582 A | 10/1997 | Bowie et al. | 435/518 |
| 5,684,711 A | 11/1997 | Agrafiotis et al. | 364/500 |
| 5,703,792 A | 12/1997 | Chapman | 364/496 |
| 5,712,171 A | 1/1998 | Zambias et al. | 436/518 |

(Continued)

FOREIGN PATENT DOCUMENTS

EP    0 355 266 B1    2/1990

(Continued)

OTHER PUBLICATIONS

Agrafiotis et al. Nonlinear Mapping Network J. Chem. Inf. Comput. Sci. Nov.-Dec. 2000, vol. 40, p. 1356-1362.*

(Continued)

*Primary Examiner*—Mary K. Zeman
(74) *Attorney, Agent, or Firm*—Wilson, Sonsini, Goodrich & Rosati

(57) ABSTRACT

The invention provides for in silico analysis of a virtual combinatorial library. Mapping coordinates for a training subset of products in the combinatorial library, and features of their building blocks, are obtained. A supervised machine learning approach is used to infer a mapping function $f$ that transforms the building block features for each product in the training subset of products to the corresponding mapping coordinates for each product in the training subset of products. The mapping function $f$ is then encoded in a computer readable medium. The mapping function $f$ can be retrieved and used to generate mapping coordinates for any product in the combinatorial library from the building block features associated with the product.

25 Claims, 8 Drawing Sheets

U.S. PATENT DOCUMENTS

| | | | |
|---|---|---|---|
| 5,712,564 A | 1/1998 | Hayosh | 324/210 |
| 5,734,796 A | 3/1998 | Pao | 395/22 |
| 5,736,412 A | 4/1998 | Zambias et al. | 436/518 |
| 5,740,326 A | 4/1998 | Boulet et al. | 395/27 |
| 5,789,160 A | 8/1998 | Eaton et al. | 435/6 |
| 5,807,754 A | 9/1998 | Zambias et al. | 436/578 |
| 5,811,241 A | 9/1998 | Goodfellow et al. | 435/7.1 |
| 5,832,494 A | 11/1998 | Egger et al. | 707/102 |
| 5,858,660 A | 1/1999 | Eaton et al. | 435/6 |
| 5,861,532 A | 1/1999 | Brown et al. | 564/123 |
| 5,866,334 A | 2/1999 | Beutel | 435/6 |
| 5,901,069 A | 5/1999 | Agrafiotis et al. | 364/528.03 |
| 5,908,960 A | 6/1999 | Newlander | 564/177 |
| 5,933,819 A | 8/1999 | Skolnick et al. | 706/21 |
| 6,014,661 A | 1/2000 | Ahlberg et al. | 707/3 |
| 6,026,397 A | 2/2000 | Sheppard | 707/5 |
| 6,037,135 A | 3/2000 | Kubo et al. | 435/7.24 |
| 6,049,797 A | 4/2000 | Guha et al. | 707/6 |
| 6,185,506 B1 | 2/2001 | Cramer et al. | 702/19 |
| 6,240,374 B1 | 5/2001 | Cramer et al. | |
| 6,295,514 B1 | 9/2001 | Agrafiotis et al. | |

FOREIGN PATENT DOCUMENTS

| | | |
|---|---|---|
| EP | 0 355 628 B1 | 2/1990 |
| EP | 0 770 876 A1 | 5/1997 |
| EP | 0 818 744 A2 | 1/1998 |
| WO | WO 91/19735 | 12/1991 |
| WO | WO 92/00091 | 1/1992 |
| WO | WO 93/20242 | 10/1993 |
| WO | WO 94/28504 | 12/1994 |
| WO | WO 95/01606 | 1/1995 |
| WO | WO 97/09342 | 3/1997 |
| WO | WO 97/20952 | 6/1997 |
| WO | WO 97/27559 | 7/1997 |
| WO | WO 98/20437 | 5/1998 |
| WO | WO 98/20459 | 5/1998 |
| WO | WO 99/35599 | 7/1999 |

OTHER PUBLICATIONS

Cohen et al. "Molecular Modeling Software and Methods for Medicinal Chemistry," *J. of Med. Chem.*, vol. 33, No. 3, pp. 883-894 (Mar. 1990).

Linusson et al., "Statistical Molecular Design of Building Blocks for Combinatorial Chemistry," *J. Med. Chem.*, vol. 43, No. 7, pp. 1320-1328 (Mar. 2000).

Rotstein et al., "GroupBuild: A Fragment-Based Method for De Novo Drug Design," *J. Med. Chem.*, vol. 36, No. 12, pp. 1700-1710 (Jun. 1993).

Borg, Ingwer and Groenen, Patrick, *Modern Multidimensional Scaling Theory and Applications*, Springer Series in Statistics, 1997, entire book submitted.

Agrafiotis, D.K. et al., "Advances in diversity profiling and combinatorial series design," *Molecular Diversity*, Kluwer Academic Publishers, vol. 4, 1999, pp. 1-22.

Agrafiotis, D.K. and Lobanov, V.S., "An Efficient Implementation of Distance-Based Diveristy Measures Based on k-d Trees," *Journal of Chemical Information and Computer Science*, American Chemical Society, vol. 39, No. 1, Jan./Feb. 1999, pp. 51-58.

Agrafiotis, D.K. and Lobanov, V.S., "Bridging The Gap Between Diversity And QSAR," *Abstracts of Papers Part 1: 215th ACS National Meeting*, American Chemical Society, Mar. 29-Apr. 2, 1998, p. 181-COMP.

Agrafiotis, D.K. and Jaeger, E.P., "Directed Diversity®: An Operating System For Combinatorial Chemistry," *Abstracts of Papers Part 1: 211th ACS National Meeting*, American Chemical Society, Mar. 24-28, 1996, p. 46-COMP.

Agrafiotis, D.K., "Diversity of Chemical Libraries," *Encyclopedia of Computational Chemistry*, John Wiley & Sons Ltd, vol. 1:A-D, 1998, pp. 742-761.

Agrafiotis, D.K., "On the Use of Information Theory for Assessing Molecular Diversity," *Journal of Chemical Information and Computer Science*, American Chemical Society, vol. 37, No. 3, May/Jun. 1997, pp. 576-580.

Agrafiotis, D.K. et al., "Parallel QSAR," *Abstracts of Papers Part 1: 217th ACS National Meeting*, Mar. 21-25, 1999, p. 50-COMP.

Agrafiotis, D.K. et al., "PRODEN: A New Program for Calculating Integrated Projected Populations," *Journal of Computational Chemistry*, John Wiley & Sons, Inc., vol. 11, No. 9, Oct. 1990, pp. 1101-1110.

Agrafiotis, D.K. and Jaeger, E.P., "Stochastic Algorithms for Exploring Molecular Diversity," *Abstracts of Papers Part 1: 213th ACS National Meeting*, American Chemical Society, Apr. 13-17, 1997, p. 16-CINF.

Agrafiotis, D., "Theoretical Aspects of the Complex: Arts and New Technologies," *Applications and Impacts Information Processing '94*, North-Holland, vol. II, 1994, pp. 714-719.

Biswas, G. et al., "Evaluation of Projection Algorithms," *IEEE Transactions On Pattern Analysis And Machine Intelligence*, IEEE Computer Society, vol. PAMI-3, No. 6, Nov. 1981, pp. 701-708.

Bonchev, D. and Trinajstić, N., "Information theory, distance matrix, and moecular branching," *The Journal of Chemical Physics*, American Institute of Physics, vol. 67, No. 10, Nov. 15, 1977, pp. 4517, 4520-4533.

Chang, C.L. and Lee, R.C.T., "A Heuristic Relaxation Method for Nonlinear Mapping in Cluster Analysis," *IEEE Transactions on Systems, Man, and Cybernetics*, IEEE Systems, Man, and Cybernetics Society, vol. SMC-3, Mar. 1973, pp. 197-200.

Cramer, R.D. et al., "Virtual Compound Libraries: A New Approach to Decision Making in Molecular Discovery Research," *J. Chem. Inf. Comput. Sci.*, American Chemical Society, vol. 38, No. 6, Nov./Dec. 1998, pp. 1010-1023.

DeMers, D. and Cottrell, G., "Non-Linear Dimensionality Reduction," *Advances in Neural Information Processing Systems*, vol. 5, 1993, pp. 580-587.

Frey, P.W. and Slate, D.J., "Letter Recognition Using Holland-Style Adaptive Classifiers," *Machine Learning*, Kluwer Academic Publishers, vol. 6, 1991, pp. 161-182.

Friedman, J.H., "Exploratory Projection Pursuit," *Journal of the American Statistical Association*, American Statistical Association, vol. 82, No. 397, Mar. 1987, pp. 249-266.

Friedman, J.H. and Tukey, J.W., "A Projection Pursuit Algorithm for Exploratory Data Analysis," *IEEE Transactions on Computers*, IEEE Computer Society, vol. C-23, No. 9, Sep. 1974, pp. 881-889.

Garrido, L. et al., "Use of Multilayer Feedforward Neural Nets As A Display Method for Multidimensional Distributions," *International Journal of Neural Systems*, World Scientific Publishing Co. Pte. Ltd., vol. 6, No. 3, Sep. 1995, pp. 273-282.

Ghose, A.K. et al., "Prediction of Hydrophobic (Lipophilic) Properties of Small Organic Molecules Using Fragmental Methods: An Analysis of ALOGP and CLOGP Methods," *Journal of Physical Chemistry*, American Chemical Society, vol. 102, No. 21, May 21, 1998, pp. 3762-3772.

Hall, L.H. and Kier, L.B., "The Molecular Connectivity Chi Indexes and Kappa Shape Indexes in Structure-Property Modeling," *Reviews in Computational Chemistry: Advances,* VCH Publishers, Inc., 1991, pp. 367-422.

Hecht-Nielsen, R., "Replicator Neural Networks for Universal Optimal Source Coding," *Science,* American Association for the Advancement of Science, vol. 269, Sep. 29, 1995, pp. 1860-1863.

Hotelling, H., "Analysis of a Complex of Statistical Variables into Principal Components," *The Journal of Educational Psychology,* Warwick and York, Inc., vol. XXIV, No. 6, Sep. 1933, pp. 417-441.

Hotelling, H., "Analysis of a Complex of Statistical Variables into Principal Components," *The Journal of Educational Psychology,* Warwick and York, Inc., vol. XXIV, No. 7, Oct. 1933, pp. 498-520.

Lee, R.C.T. et al., "A Triangulation Method for the Sequential Mapping of Points from N-Space to Two-Space," *IEEE Transactions on Computers,* The Institute of Electrical and Electronics Engineers, Mar. 1977, pp. 288-292.

Lipinski, C.A. et al., "Experimental and computational approaches to estimate solubility and permeability in drug discovery and development settings," *Advanced Drug Delivery Reviews,* Elsevier Science B.V., vol. 23, 1997, pp. 3-25.

Lobanov, V.S. and Agrafiotis, D.K., "Intelligent Database Mining Techniques," *Abstracts of Papers Part 1: 215th ACS National Meeting,* Mar. 29-Apr. 2, 1998, p. 19-COMP.

Lobanov, V.S. et al., "Rational Selections from Virtual Libraries," *Abstracts of Papers Part 1: 217th ACS National Meeting,* Mar. 21-25, 1999, p. 181-COMP.

Mao, J. and Jain, A.K., "Artificial Neural Networks for Feature Extraction and Multivariate Data Projection," *IEEE transactions on Neural Networks,* IEEE Neural Networks, vol. 6, No. 2, Mar. 1995, pp. 296-317.

Oja, E., "Principal Components, Minor Components, and Linear Neural Networks," *Neural Networks,* Pergamon Press Ltd., vol. 5, 1992, pp. 927-935.

Patterson, D.E. et al., "Neighborhood Behavior: A Useful Concept for Validation of 'Molecular Diversity' Descriptors," *Journal of Medicinal Chemistry,* American Chemical Society, vol. 39, No. 16, 1996, pp. 3049-3059.

Pykett, C.E., "Improving the Efficiency of Sammon's Nonlinear Mapping by Using Clustering Archetypes," *Electronics Letters,* The Institution of Electrical Engineers, vol. 14, No. 25, Dec. 7, 1978, pp. 799-800.

Rubner, J. and Tavan, P., "A Self-Organizing Network for Principal-Component Analysis," *Europhysics Letters,* European Physical Society, vol. 10, No. 7, Dec. 1, 1989, pp. 693-698.

Sadowski, J. et al., "Assessing Similarity and Diversity of Combinatorial Libraries by Spatial Autocorrelation Functions and Neural Networks," *Angewandte Chemie,* VCH, vol. 34, No. 23/24, Jan. 5, 1996, pp. 2674-2677.

Thompson, L.A. and Ellman, J.A., "Synthesis and Applications of Small Molecule Libraries," *Chemical Reviews,* American Chemical Society, vol. 96, No. 1, Jan./Feb. 1996, pp. 555-585, 588-600.

Barnard, John M. and Downs, Geoff M., "Computer representation and manipulation of combinatorial libraries," *Perspectives in Drug Discovery and Design,* Kluwer Academic Publishers, 1997, pp. 13-30.

Brint, Andrew T. and Willett, Peter, "Upperbound procedures for the identification of similar three-dimensional chemical structures," *Journal of Computer-Aided Molecular Design,* ESCOM Science Publishers B.V., vol. 2, No. 4, Jan. 1989, pp. 311-320.

Brown, Robert D. and Martin, Yvonne C., "Designing Combinatorial Library Mixtures Using a Genetic Algorithm," *Journal of Medicinal Chemistry,* American Chemical Society, vol. 40, No. 15, 1997, pp. 2304-2313.

Kim, J. et al., "Multiple Neural Networks using the Reduced Input Dimension," *Proceedings of the International Conference on Acoustics, Speech, and Signal Processing,* IEEE, vol. 2, Apr. 19-22, 1994, pp. II-601 to II-604.

Gillet, Valerie J. et al., "Selecting Combinatorial Libraries to Optimize Diversity and Physical Properties," *Journal of Chemical Information and Computer Sciences,* American Chemical Society, vol. 39, No. 1, 1999, pp. 169-177.

Kearsley, Simon K. et al., "Chemical Similarity Using Physiochemical Property Descriptors," *Journal of Chemical Information and Computer Sciences,* American Chemical Society, vol. 36, No. 1, 1996, pp. 118-127.

Leland, Burton A, et al., "Managing the Combinatorial Explosion," *Journal of Chemical Information and Computer Sciences,* American Chemical Society, vol. 37, No. 1, 1997, pp. 62-70.

Lewis, Richard A. et al., "Similarity Measures for Rational Set Selection and Analysis of Combinatorial Libraries: The Diverse Property-Derived (DPD) Approach," *Journal of Chemical Information and Computer Sciences,* American Chemical Society, vol. 37, No. 3, 1997, pp. 599-614.

Martin, Eric J. and Critchlow, Roger E., "Beyond Mere Diversity: Tailoring Combinatorial Libraries for Drug Discovery," *Journal of Combinatorial Chemistry,* American Chemical Society, vol. 1, No. 1, 1999, pp. 32-45.

Sheridan, Robert P. et al., "Chemical Similarity Using Geometric Atom Pair Descriptors," *Journal of Chemical Information and Computer Sciences,* American Chemical Society, vol. 36, No. 1, 1996, pp. 128-136.

Willett, Peter et al., "Chemical Similarity Searching, " *Journal of Chemical Information and Computer Sciences,* American Chemical Society, vol. 38, No. 6, 1998, pp. 983-996.

Agrafiotis, Dimitris K. and Lobanov, Victor S., "Ultrafast Algorithm for Designing Focused Combinational Arrays," *Journal of Chemical Information and Computer Sciences,* American Chemical Society, 2000, vol. 40, No. 4, pp. 1030-1038.

Ajay et al., "Can We Learn To Distinguish between 'Drug-Like' and 'Nondrug-like' Molecules?" *J. Med. Chem.,* 1998, American Chemical Society, vol. 41, No. 18, pp. 3314-3324.

English-language Abstract of European Patent No. 0 355 628, printed from Dialog File No. 351(Feb. 1990—Date of publication of application), 2 pages.

Brown, Robert D. and Martin, Yvonne C., "The Information Content of 2D and 3D Structural Descriptors Relevant to Ligand-Receptor Binding," *Journal of Chemical Information and Computer Sciences,* American Chemical Society, 1997, vol. 37, No. 1, pp. 1-9.

Brown, Robert D. and Martin, Yvonne C., "Use of Structure-Activity Data To Compare Structure-Based Clustering Methods and Descriptors for Use in Compound Selection," *Journal of Chemical Information and Computer Sciences,* American Chemical Society, 1996, vol. 36, No. 3, pp. 572-584.

Cummins, David J. et al., "Molecular Diversity in Chemical Databases: Comparison of Medicinal Chemistry Knowledge Bases and Databases of Commerically Available Compounds," *Journal Chemical Information and Computer Sci-*

*ences,* American Chemical Society, 1996, vol. 36, No. 4, pp. 750-763.

Domine, D. et al., "Non-Linear Mapping for Structure-Activity and Structure-Property Modeling," *Journal of Chemometrics,* John Wiley & Sons, Ltd., vol. 7, No. 4, Jul.-Aug. 1993, pp. 227-242.

Havel, T., "A New Method for Building Protein Conformations from Sequence Alignments with Homologues of Known Structure," *Journal of Molecular Biology,* Academic Press Limited, vol. 217, No. 1, Jan. 5, 1991, pp. 1-7.

Downs, Geoff M. and Barnard, John M., "Techniques for Generating Descriptive Fingerprints in Combinatorial Libaries," *Journal of Chemical Information and Computer Sciences,* American Chemical Society, 1997, vol. 37, No. 1, pp. 59-61.

Gillet, Valerie J., "Background Theory of Molecular Diversity," *Molecular Diversity in Drug Design,* Kluwer Academic Publishers, 1999, pp. 43-65.

Good, Andrew C. and Lewis, Richard A., "New Methodology for Profiling Combinatorial Libraries and Screening Sets: Cleaning Up the Design Process with HARPick," *Journal of Medicinal Chemistry,* American Chemical Society, 1997, vol. 40, No. 24, pp. 3926-3936.

Pal, N.R. and Eluri, V.K., "Two Efficient Connectionist Schemes for Structure Preserving Dimensionality Reduction," *IEEE Transactions on Neural Networks,* IEEE, vol. 9, No. 6, Nov. 1998, pp. 1142-1154.

Jamois, Eric A. et al., "Evaluation of Reagent-Based and Product-Based Strategies in the Design of Combinatorial Library Subsets," *Journal of Chemical Information and Computer Sciences,* American Chemical Society, 2000, vol. 40, No. 1, pp. 63-70.

Kim, H. et al., "Self-Organized Distributed Networks for Learning Highly Nonlinear Mapping," *Intelligent Engineering Systems Through Artificial Neural Networks,* American Society of Mechanical Engineers, vol. 4, Nov. 13-16, 1994, pp. 109-114.

Leach, Andrew R. et al., "Implementation of a System for Reagent Selection and Library Enumeration, Profiling, and Design," *Journal of Chemical Information and Computer Sciences,* American Chemical Society, 1999, vol. 39, No. 6, pp. 1161-1172.

Lobanov, Victor S. and Agrafiotis, Dimitris K., "Stochastic Similarity Selections from Large Combinatorial Libraries," *Journal of Chemical Information and Computer Sciences,* American Chemical Society, Mar./Apr. 2000, vol. 40, No. 2, pp. 460-470.

Matter, Hans and Pötter, Thorsten, "Comparing 3D Pharmacophore Triplets and 2D Fingerprints for Selecting Diverse Compound Subsets," *Journal of Chemical Information and Computer Sciences,* American Chemical Society, 1999, vol. 39, No. 6, pp. 1211-1225.

Matter, Hans, "Selecting Optimally Diverse Compounds from Structure Databases: A Validation Study of Two-Dimensional and Three-Dimensional Molecular Descriptors," *Journal of Medicinal Chemistry,* American Chemical Society, 1997, vol. 40, No. 8, pp. 1219-1229.

Sadowski, Jens and Kubinyi, Hugo, "A Scoring Scheme for Discriminating between Drugs and Nondrugs," *Journal of Medicinal Chemistry,* American Chemical Society, 1998, vol. 41, No. 18, pp. 3325-3329.

Schnur, Dora, "Design and Diversity Analysis of Large Combinatorial Libraries Using Cell-Based Methods," *Journal of Chemical Information and Computer Science,* American Chemical Society, 1999, vol. 39, No. 1, pp. 36-45.

Schuffenhauer, Ansgar et al., "Similarity Searching in Files of Three-Dimensional Chemical Structures: Analysis of the BIOSTER Database Using Two-Dimensional Fingerprints and Molecular Field Descriptors," *Journal of Chemical Information and Computer Science,* American Chemical Society, 2000, vol. 40, No. 2, pp. 295-307.

Turner, David B. et al., "Rapid Quantification of Molecular Diversity for Selective Database Acquistion," *Journal of Chemical Information and Computer Science,* American Chemical Society, 1997, vol. 37, No. 1, pp. 18-22.

Wang, Jing and Ramnarayan, Kal, "Toward Designing Drug-Like Libraries: A Novel Computational Approach for Prediction of Drug Feasibility of Compounds," *Journal of Combinatorial Chemistry,* American Chemical Society, Nov./Dec. 1999, vol. 1, No. 6, pp. 524-533.

Gasteiger, J. et al, "Assessment of the Diversity of Combinatorial Libraries by an Encoding of Molecular Surface Properties," *Abstracts of Papers Part 1: 211th ACS National Meeting,* Mar. 24-28, 1996, p. 70-CINF.

Hassan, Moises et al., "Optimization and visualization of molecular diversity of combinatorial libraries," *Molecular Diversity,* ESCOM Science Publishers B.V., 1996, vol. 2, pp. 64-74.

Bellman, R.E., *Adaptive Control Processes: A Guided Tour,* Princeton Univ. Press, Princeton, NJ (1961), entire book submitted.

Bezdek, J.C., *Pattern Recognition with Fuzzy Objective Function Algorithms,* Plenum Press, New York, NY (1981), entire book submitted.

Johnson, M.A., and Maggiora, G.M., *Concept and Applications of Molecular Similarity,* John Wiley and Sons, New York, NY (1990), entire book submitted.

Kohonen, T., *Self-Organizing Maps,* Springer-Verlag, Heidelberg, Germany (1995), entire book submitted.

Oja, E., *Subspace Methods of Pattern Recognition,* Research Studies Press Ltd., Letchworth, England (1983), entire book submitted.

Agrafiotis, D.K., "A New Method For Analyzing Protein Sequence Relationships Based On Sammon Maps," *Protein Science,* Cambridge University Press, vol. 6, No. 2, Feb. 1997, pp. 287-293.

Spellmeyer, D. et al., "Conformational analysis using distance geometry methods," *Journal of Molecular Graphics & Modelling,* Elsevier Science, Inc., vol. 15, No. 1, Feb. 1997, pp. 18-36.

Amzel, L.M., "Structure-based drug design," *Current Opinion in Biotechnology,* vol. 9, No. 4, Aug. 1998, pp. 366-369.

Blaney, J.M. and Martin, E.J., "Computational approaches for combinatorial library design and molecular diversity analysis," *Current Opinion in Chemical Biology,* Current Biology Ltd., vol. 1, No. 1, Jun. 1997, pp. 54-59.

Saunders, M. , "Stochastic Exploration of Molecular Mechanics Energy Surfaces. Hunting for the Global Minimum," *Journal of the American Chemical Society,* American Chemical Society, vol. 109, 10, May 13, 1987, pp. 3150-3152.

Caflisch, A. and Karplus, M., "Computational combinatorial chemistry for de novo ligand design: Review and assessment," *Perspectives in Drug Discovery and Design,* ESCOM Science Publishers B.V., vol. 3, 1995, pp. 51-84.

Porto, V. et al., "Alternative Neural Network Training Methods," *IEEE Expert,* IEEE, vol. 10, No. 4, pp. 16-22.

Eichler, U. et al., "Addressing the problem of molecular diversity," *Drugs of the Future,* Prous Science, vol. 24, No. 2, 1999, pp. 177-190.

Felder, E.R. and Poppinger, D., "Combinatorial Compound Libraries for Enhanced Drug Discovery Approaches," *Advances in Drug Research,* Academic Press, vol. 30, 1997, pp. 112-199.

Geysen, H.M. and Mason, T.J., "Screening Chemically Synthesized Peptide Libraries for Biologically-Relevant Molecules," *Bioorganic & Medicinal Chemistry Letters,* Pergamon Press Ltd., vol. 3, No. 3, 1993, p. 397-404.

Gobbi, A. et al., "New Leads By Selective Screening of Compounds From Large Databases," *Abstracts of Papers Part 1: 213th ACS National Meeting,* American Chemical Society, Apr. 13-17, 1997, p. 67-CINF.

Houghten, R.A. et al., "The Use of Synthetic Peptide Combinatorial Libraries for the Identification of Bioactive Peptides," *Peptide Research,* vol. 5, No. 6, 1992, pp. 351-358.

Klopman, G., "Artificial Intelligence Approach to Structure-Activity Studies. Computer Automated Structure Evaluation of Biological Activity of Organic Molecules," *Journal of the American Chemical Society,* American Chemical Society, vol 106, No. 24, 1984, pp. 7315-7321.

Lajiness, M.S. et al., "Implementing Drug Screening Programs Using Molecular Similarity Methods," *QSAR: Quantitative Structure-Activity Relationships in Drug Design,* Alan R. Liss, Inc., 1989, pp. 173-176.

Loew, G.H. et al., "Strategies for Indirect Computer-Aided Drug Design," *Pharmaceutical Research,* Plenum Publishing Corporation, vol. 10, No. 4, 1993, pp. 475-486.

Lynch, M.F. et al., "Generic Structure Storage and Retrieval," *Journal of Chemical Information and Computer Sciences,* American Chemical Society, vol. 25, No. 3, Aug. 1985, pp. 264-270.

Myers, P.L. et al., "Rapid Reliable Drug Discovery," *Today's Chemist At Work,* American Chemical Society, vol. 6, No. 7, Jul./Aug. 1997, pp. 46-48, 51 & 53.

Pabo, C.O. and Suchanek, E.G., "Computer-Aided Model-Building Strategies for Protein Design," *Biochemistry,* American Chemical Society, vol. 25, No. 20, 1986, pp. 5987-5991.

Saudek, V. et al., "Solution Conformation of Endothelin-1 by H NMR, CD, and Molecular Modeling," *International Journal of Peptide Protein Research,* Munksgaard International Publishers Ltd., vol. 37, No. 3, 1991, pp. 174-179.

Singh, J. et al., "Application of Genetic Algorithms to Combinatorial Synthesis: A Computational Approach to Lead Identification and Lead Optimization," *J. Am. Chem. Soc.,* American Chemical Society, vol. 118, No. 7, Feb. 7, 1996, pp. 1669-1676.

Van Drie, J.H. and Lajiness, M.S., "Approaches to virtual library design," *Drug Discovery today,* Elsevier Science Ltd., vol. 3, No. 6, Jun. 1998, pp. 274-283.

Walters, W.P. et al., "Virtual screening—an overview," *Drug Discovery today,* Elsevier Science Ltd., vol. 3, No. 4, Apr. 1998, pp. 160-178.

Weber, L., "Evolutionary combinatorial chemistry: application of genetic algorithms," *Drug Discovery today,* Elsevier Science Ltd., vol. 3, No. 8, Aug. 1998, pp. 379-385.

Weber, L. et al., "Optimization of the Biological Activity of Combinatorial Compound Libraries by a Genetic Algorithm," *Angewandte Chemie International Edition in English,* VCH, vol. 34, No. 20, Nov. 3, 1995, pp. 2280-2282.

Graybill, T.L. et al., "Enhancing the Drug Discovery Process by Integration of High-Throughput Chemistry and Structure-Based Drug Design," Molecular Diversity and Combinatorial Chemistry: Libraries and Drug Discovery, American Chemical Society, 1996, pp. 16-27.

Saund, E., "Dimensionality-Reduction Using Connectionist Networks," *IEEE Transactions on Pattern Analysis and Machine Intelligence,* IEEE, vol. 11, No. 3, Mar. 1989, pp. 304-314.

"3DP gains drug research patent", *Chemistry in Britain,* The Royal Society of Chemistry, vol. 32, No. 1, Jan. 1996, p. 22.

"Accelerate the Discovery Cycle with Chem-X!", Source and date of publication unclear, 2 pages.

Agrafiotis, D. K., "Stochastic Alogorithms for Maximizing Molecular Diversity", *Journal of Chemical Information and Computer Sciences,* American Chemical Society, vol. 37, No. 5, 1997, pp. 841-851.

Alsberg, B.K. et al., "Classification of pyrolysis mass spectra by fuzzy multivariate rule induction-comparison with regression, K-nearest neighbour, neural and decision-tree methods", *Analytica Chimica Acta,* Elsevier Science B.V., vol. 348, No. 1-3, Aug. 20, 1997, pp. 389-407.

Andrea, T.A. and Kalayeh, H., "Applications of Neural Networks in Quantitative Structure-Activity Relationships of Dihydrofolate Reductase Inhibitors", *Journal of Medicinal Chemistry,* American Chemical Society, vol. 34, No. 9, 1991, pp. 2824-2836.

Aoyama, T. et al., "Neural Networks Applied to Quantitative Structure-Activity Relationship Analysis", *Journal of Medicinal Chemistry,* American Chemical Society, vol. 33, No. 9, 1990, pp. 2583-2590.

Aoyama, T. and Ichikawa, H., "Obtaining the Correlation Indices between Drug Activity and Structural Parameters Using a Neural Network", *Chemical & Pharamaceutical Bulletin,* Pharmaceutical Society of Japan, vol. 39, No. 2, Feb. 1991, pp. 372-378.

Mumenthaler, Ch. And Braun, W., "Automated Assignment of Simulated and Experimental NOESY Spectra of Proteins by Feedback Filtering and Self-correcting Distance Geometry," *Journal of Molecular Biology,* Academic Press Limited, vol. 254, No. 3, Dec. 1, 1995, pp. 465-480.

Baum, R.M., "Combinatorial Approaches Provide Fresh Leads for Medicinal Chemistry", *Chemical & Engineering News,* American Chemical Society, Feb. 7, 1994, pp. 20-26.

Bentley, J. L., "Multidimensional Binary Search Trees Used for Associative Searching", *Communications of the ACM,* Association for Computing Machinery, Inc., vol. 18, No. 9, Sep. 1975, pp. 509-517.

Bottou, L. and Vapnik, V. "Local Learning Algorithms", *Neural Computation,* Massachusetts Institute of Technology, vol. 4, No. 6, Nov. 1992, pp. 888-900.

Boulu, L.G. and Crippen, G.M., "Voronoi Binding Site Models: Calculation of Binding Modes and Influence of Drug Binding Data Accuracy", *Journal of Computational Chemistry,* John Wiley & Sons, Inc., vol. 10, No. 5, Jul./Aug. 1989, pp. 673-682.

Boulu, L.G. et al., "Voronoi Binding Site Model of a Polycyclic Aromatic Hydrocarbon Binding Protein", *Journal of Medicinal Chemistry,* American Chemical Society, vol. 33, No. 2, 1990, pp. 771-775.

Cacoullos, T., "Estimation of a Multivariate Density", *Annals of The Institute of Statistical Mathematics,* The Institute of Statistical Mathematics, vol. 18, No. 2, 1966, pp. 179-189.

Clark, R.D., "OptiSim: An Extended Dissimilarity Selection Method for Finding Diverse Representative Subsets", *Journal of Chemical Information and Computer Science,* American Chemical Society, vol. 37, No. 6, 1997, pp. 1181-1188.

Clark, D. E., and Westhead, D.R., "Evolutionary algorithms in computer-aided molecular design", *Journal of Computer-Aided Molecular Design,* ESCOM Science Publishers B.V., vol. 10, No. 4, Aug. 1996, pp. 337-358.

Cramer, III, R. D. et al., "Comparative Molecular Field Analysis (CoMFA). 1. Effect of Shape on Binding of Steroids to Carrier Proteins", *Journal of The American Chemical Society,* American Chemical Society, vol. 110, No. 18, Aug. 31, 1988, pp. 5959-5967.

Cramer, III, R. D. et al., "Substructural Analysis. A Novel Approach to the Problem of Drug Design", *Journal of Medicinal Chemistry,* vol. 17, No. 5, May 1974, pp. 533-535.

Crippen, G. M., "Voronoi Binding Site Models", *Journal of Computational Chemistry,* John Wiley & Sons, Inc., vol. 8, No. 7, Oct./Nov. 1987, pp. 943-955.

Friedman, J. H. et al., "An Algorithm for Finding Best Matches in Logarithmic Expected Time", *ACM Transactions on Mathematical Software,* Association for Computing Machinery, vol. 3, No. 3, No. 3, Sep. 1977, pp. 209-226.

Friedman, J.H., "Fitting Functions To Noisy Data In High Dimensions", Department of Statistics- Stanford University Technical Report No. 101, (Aug., 1988), pp. 1-36.

Gallop, M. A. et al., "Applications of Combinatorial Technologies to Drug Discovery. 1. Background and Peptide Combinatorial Libraries", *Journal of Medicinal Chemistry,* American Chemical Society, vol. 37, No. 9, Apr. 29, 1994, pp. 1233-1251.

Ghose, A. K. and Crippen, G.M., "Use of Physicochemical Parameters in Distance Geometry and Related Three-Dimensional Quantitative Structure-Activity Relationships: A Demonstration Using *Escherichia coli* Dihydrofolate Reductase Inhibitors", *Journal of Medicinal Chemistry,* American Chemical Society, vol. 28, No. 3, 1985, pp. 333-346.

Good, A. C. et al., "Structure-Activity Relationships from Molecular Similarity Matrices", *Journal of Medicinal Chemistry,* American Chemical Society, vol. 36, No. 4, Feb. 19, 1993, pp. 433-438.

Gordon, E. M. et al., "Applications of Combinatorial Technologies to Drug Discovery. 2. Combinatorial Organic Synthesis, Library Screening Strategies, and Future Directions", *Journal of Medicinal Chemistry,* American Chemical Society, vol. 37, No. 10, May 13, 1994, pp. 1385-1401.

Hartigan, J. A., "Representation of Similarity Matrices By Trees", *Journal of the American Statistical Association,* vol. 62, No. 320, Dec., 1967, pp. 1140-1158.

Hopfinger, A. J., "A QSAR Investigation of Dihydrofolate Reductase Inhibition by Baker Triazines Based upon Molecular Shape Analysis", *Journal of the American Chemical Society,* American Chemical Society, vol. 102, No. 24, Nov. 19, 1980, pp. 7196-7206.

Jackson, R. C., "Update on computer-aided drug design", *Current Opinion in BIOTECHNOLOGY,* Current Biology Ltd., vol. 6, No. 6, Dec. 1995, pp. 646-651.

Kim, K. H., "Comparative molecular field analysis (CoMFA)", *Molecular Similarity in Drug Design,* ed. P. M. Dean, Blackie Academic & Professional, 1995, Ch. 12, pp. 291-331.

Kohonen, T., "Self-Organized Formation of Topologically Correct Feature Maps", *Biological Cybernetics,* Springer-Verlag, vol. 43, No. 1, 1982, pp. 59-69.

Koile, K. and Shapiro, R., "Building A Collaborative Drug Design System", *Proceedings of the 25h Hawaii International Conference on System Sciences,* IEEE, 1992, pp. 706-716.

Kowalski, B. R. and Bender, C. F., "Pattern Recognition. II. Linear and Nonlinear Methods for Displaying Chemical Data", *Journal of the American Chemical Society,* American Chemical Society, vol. 95, No. 3, Feb. 7, 1973, pp. 686-693.

Kruskal, J. B., "Nonmetric Multidimensional Scaling: A Numerical Method", *Psychometrika,* vol. 29, No. 2, Jun. 1964, pp. 115-129.

Lengauer, T. and Rarey, M., "Computational methods for biomolecular docking", *Current Opinion in Structural Biology,* Current Biology Ltd, vol. 6, No. 3, Jun., 1996, pp. 402-406.

Luke, B. T., "Evolutionary Programming Applied to the Development of Quantitative Structure-Activity Relationships and Quantitative Structure-Property Relationships", *Journal of Chemical Information and Computer Sciences,* American Chemical Society, vol. 34, No. 6, Nov./Dec. 1994, pp. 1279-1287.

Martin, E. J. et al., "Does Combinatorial Chemistry Obviate Computer-Aided Drug Design?", *Reviews in Computational Chemistry,* VCH Publishers, Inc., vol. 10, 1997, pp. 75-99.

Martin, E. J. et al., "Measuring Diversity: Experimental Design of Combinatorial Libraries for Drug Discovery", *Journal of Medicinal Chemistry,* American Chemical Society, vol. 38, No. 9, Apr. 28, 1995, pp. 1431-1436.

McMartin, C. and Bohacek, R.S., "QXP: Powerful, rapid computer algorithms for structure-based drug design", *Journal of Computer-Aided Molecular Design,* Kluwer Academic Publishers, vol. 11, No. 4, Jul. 1997, pp. 333-344.

Mezey, P. G. and Walker, P.D., "Fuzzy molecular fragments in drug research", *Drug Discovery today,* vol. 2, No. 4, Apr. 1997, pp. 132-137.

Müller, K., "On the paradigm shift from rational to random design", *Journal of Molecular Structure (Theochem),* Elsevier Science B.V., vol. 398-399, Special Issue, 1997, pp. 467-471.

Havel, T. and Wüthrich, K., "An Evaluation of the Combined Use of Nuclear Magnetic Resonance and Distance Geometry for the Determination of Protein Conformations in Solutions," *Journal of Molecular Biology,* Academic Press Inc., vol. 182, No. 2, Mar. 20, 1985, pp. 281-294.

Meng, E. et al., "Orientational Sampling and Ragid-Body Minimization in Molecular Docking," *PROTEINS: Structure, Function and Genetics,* Wiley-Liss, Inc., vol. 17, No. 3, 1993, pp. 266-278.

Omohundro, S. M., "Bumptrees for Efficient Function, Constraint, and Classification Learning", *Advances in Neural Information Processing Systems 3,* Morgan Kaufmann, 1991, 7 pages, unknown.

Parrill, A. L., "Evolutionary and genetic methods in drug design", *Drug Discovery today,* Elsevier Science Ltd., vol. 1, No. 12, Dec. 1996, pp. 514-521.

Polanski, J., "A neural network for the simulation of biological systems", *Journal of Molecular Structure (Theochem).* Elsevier Science Ltd., vol. 398-399, Special Issue, 1997, pp. 565-571.

Ramos-Nino, M. E. et al., "A comparison of quantitative structure-activity relationships for the effect of benzoic and cinnamic acids on *Listeria monocytogenes* using multiple linear regression, artificial neural network and fuzzy systems", *Journal of Applied Microbiology,* Society for Applied Bacteriology, vol. 82, No. 2, Feb. 1997, pp. 168-176.

Rogers, D. and Hopfinger, A. J., "Application of Genetic Function Approximation to Quantitative Structure-Activity Relationships and Quantitative Structure-Property Relationships", *Journal of Chemical Information and Computer Sciences,* American Chemical Society, vol. 34, No. 4, Jul./Aug. 1994, pp. 854-866.

Sammon, Jr., J. W., "Nonlinear Mapping for Data Structure Analysis", *IEEE Transactions on Computers,* IEEE, vol. C-18, No. 5, May 1969, pp. 401-409.

Simon, Z. et al., "Mapping of Dihydrofolate-reductase Receptor Site by Correlation with Minimal Topological (Steric) Differences", *Journal of Theoretical Biology,* Academic Press, Inc., vol. 66, No. 3, Jun. 7, 1997, pp. 485-495.

Smellie, A. S. et al., "Fast Drug-Receptor Mapping by Site-Directed Distances: A Novel Method of Predicting New Pharmacological Leads", *Journal of Chemical Information and Computer Sciences,* American Chemical Society, vol. 31, No. 3, Aug. 1991, pp. 386-392.

Specht, D. F., "A General Regression Neural Network", *IEEE Transactions on Neural Networks,* IEEE, vol. 2, No. 6, Nov. 1991, pp. 568-576.

Svozil, D. et al., "Neural Network Prediction of the Solvatochromic Polarity/Polarizability Parameter $TT^H_2$", *Journal of Chemical Information and Computer Sciences,* American Chemical Society, vol. 37, No. 2, 1997, pp. 338-342.

Todorov, N. P. and Dean, P. M., "Evaluation of a method for controlling molecular scaffold diversity in de novo ligand design", *Journal of Computer-Aided Molecular Design,* ESCOM Science Publishers B.V., vol. 11, 1997, pp. 175-192.

Torgerson, W. S., "Multidimensional Scaling: I. Theory and Method", *Psychometrika,* The Psychometric Society, vol. 17, No. 4, Dec. 1952, pp. 401-419.

Vapnik, V., "Principles of Risk Minimization for Learning Theory", *Advances in Neural Information Processing Systems 4,* Morgan Kaufmann Publishers, Inc., 1992, pp. 831-838.

Vapnik, V. and Bottou, L., "Local Algorithms for Pattern Recognition and Dependencies Estimation", *Neural Computation,* Massachusetts Institute of Technology, vol. 5, No. 6, Nov. 1993, pp. 893-909.

Viswanadhan, V. N. et al., "Mapping the binding site of the nucleoside transporter protein: a 3D-QSAR study", *Biochimica et Biophysica Acta,* Elsevier Science Publishers B.V., vol. 1039, No. 3, 1990, pp. 356-366.

Kuszewski, J. et al., "Sampling and efficiency of metric matrix, distance geometry: A novel partial metrization algorithm," *Journal of Biomolecular NMR,* Escom Science Publishers B.V., vol. 2, No. 1, Jan. 1992, pp. 33-56.

Westhead, D. R. et al., "A comparison of heuristic search algorithms for molecular docking", *Journal of Computer-Aided Molecular Design,* Kluwer Academic Publishers, vol. 11, 1997, pp. 209-228.

Willett, P., "Genetic algorithms in molecular recognition and design", *Trends in Biotechnology,* Elsevier Science Publishers B.V., vol., 13, No. 12, Dec. 1995, pp. 516-521.

Willett, P. and Winterman, V., "A Comparison of Some Measures for the Determination of Inter-Molecular Structural Similarity Measures of Inter-Molecular Structural Similarity", *Quantitative Structure-Activity Relationships,* VCH, vol. 5, No. 1, Mar. 1986, pp. 18-25.

Zadeh, L. A., "Communication Fuzzy Algorithms", *Information and Control,* Academic Press Inc., vol. 12, No. 2, Feb. 1968, pp. 94-102.

Zadeh, L. A., "Fuzzy Sets", *Information and Control,* Academic Press Inc., vol. 8, No. 3, Jun. 1965, pp. 338-353.

Jorgensen, W. and Tirado-Rives, J., "Monte Carlo vs. Molecular Dynamics for Conformational Sampling," *Journal of Physical Chemistry,* American Chemical Society, vol. 100, No. 34, Aug. 22, 1996, pp. 14508-14513.

Jain, A. et al., "Artificial Neural Networks: A Tutorial," IEEE, Mar. 1996, pp. 31-44.

Aoyama, T. et al., "Neural Networks Applied to Structure-Activity Relationships," *Journal of Medicinal Chemistry,* American Chemical Society, vol. 33., No. 3, 1990, pp. 905-908.

Gasteiger, J. et al., "Analysis of the Reactivity of Single Bonds in Aliphatic Molecules by Statistical and Pattern Recognition Methods," *Journal of Chemical Information and Computer Sciences,* American Chemical Society, vol. 33, No. 3, 1993, pp. 385-394.

Guez, A. and Nevo, I., "Neural networks and fuzzy logic in clinical laboratory computing with application to integrated monitoring," *Clinica Chimica Acta,* Elsevier Science Publishers B.V., vol. 248, 1996, pp. 73-90.

Rouvray, D.H., "Similarity in Chemistry: Past, Present and Future," *Topics in Chemistry,* Spinger-Verlag, vol. 173, 1995, pp. 1-30.

de Ridder, D. and Duin, R.P.W., "Sammon's mapping using neural networks: A comparison," *Pattern Recognition Letters,* Elsevier Science Publishers B.V., vol. 18, No. 11-13, 1997, pp. 1307-1316.

Havel, T. and Wüthrich, K., "A Distance Geometry Program for Determining the Structures of Small Proteins and other Macromolecules from Nuclear Magnetic Resonance Measurements of Intramolecular $^1H$-$^1H$ Proximities in Solution," *Bulletin of Mathematical Biology,* Pergamon Press, vol. 46, No. 4, 1984, pp. 673-698.

Chang, G. et al., An Internal Coordinate Monte Carlo Method for Searching Conformational Space, *Journal of the American Chemical Society,* American Chemical Society, vol. III, Jun. 1989, No. 12, pp. 4379-4386.

Crippen, G.M. and Havel, T.F., *Distance Geometry and Molecular Conformation,* Research Studies Press Ltd., 1988, entire book submitted.

Feuston, B. et al., "Comparison of Knowledge-Based and Distance Geometry Approaches for Generation of Molecular Conformations," *Journal of Information and Computer Sciences,* American Chemical Society, vol. 41, No. 3, 2001, pp. 754-763.

Ferguson, D. and Raber, D., "A New Approach to Probing Conformational Space with Molecular Mechanics: Random Incremental Pulse Search," *Journal of the American Chemical Society,* American Chemical Society, vol. 111, No. 12, 1989, pp. 4371-4378.

Halgren, T. and Nachbar, R., "Merck Molecular Force Field. IV. Conformational Energies and Geometries for MMFF94*," *Journal of Computational Chemistry,* John Wiley & Sons, Inc., vol. 17, Nos. 5 & 6, 1996, pp. 587-915.

Halgren, T., "Merck Molecular Force Field. V. Extension of MMFF94 Using Experimental Data, Additional Computational Data, and Empirical Rules*," *Journal of Computational Chemistry,* John Wiley & Sons, Inc., vol. 17, Nos. 5 & 6, Apr. 1996, pp. 616-641.

Huang, E. et al., "Distance geometry generates native-like folds for small helical proteins using the consensus distances of predicted protein structures," *Protein Science,* The Protein Society, vol. 7, No. 9, Sep. 1998, pp. 1998-2003.

Gillet, Valerie J. et al., "The Effectiveness of Reactant Pools for Generating Structurally-Diverse Combinatorial Librar ies," Journal of Chemical and Information Computer Sciences, American Chemical Society, vol. 37, No. 4, 1997, pp. 731-740.

Leach, A., "A Survey of Methods for Searching the Conformational Space of Small and Medium-Sized Molecules," Reviews in Computational Chemistry, VCH Publishers, vol. 2, pp. 1-55.

Havel, T., "A New Method for Building Protein Conformations from Sequence Alignments with Homologues of Known Structure," Journal of Molecular Biology, Academic Press Limited, vol. 217, No. 1, Jan. 5, 1991, pp. 1-7.

Havel, T. and Wüthrich, K., "A Distance Geometry Program for Determining the Structures of Small Proteins and other Macromolecules from Nuclear Magnetic Resonance Measurements of Intramolecular $^1H$-$^1H$ Proximities in Solution," Bulletin of Mathamatical Biology, Pergamon Press, vol. 46, No. 4, 1984, pp. 673-698.

Linusson et al., Statistical Molecular Design of Building Blocks for Combinatorial Chemistry, vol. 43, No. 7, American Chemical Society, Published on web Mar. 8, 2000, p. 1320-1328.

* cited by examiner

METHOD, SYSTEM, AND COMPUTER PROGRAM PRODUCT FOR ANALYZING COMBINATORIAL LIBRARIES

CROSS-REFERENCE TO RELATED APPLICATIONS

This application is a continuation-in-part of U.S. application Ser. No. 09/934,084, filed Aug. 22, 2001 now U.S. Pat. No. 6,834,239, which is incorporated by reference herein in its entirety, and it claims the benefit of U.S. Provisional Application No. 60/264,258, filed Jan. 29, 2001, and U.S. Provisional Application No. 60/274,238, filed Mar. 9, 2001, each of which is incorporated by reference herein in its entirety.

FIELD OF THE INVENTION

The present invention relates to combinatorial chemistry and computer aided molecular design. The present invention also relates to pattern analysis, information representation, information cartography and data mining. In particular, the present invention relates to generating mapping coordinates for products in a combinatorial chemical library based on reagent data.

BACKGROUND OF THE INVENTION

Molecular similarity is one of the most ubiquitous concepts in chemistry (Johnson, M. A., and Maggiora, G. M., *Concepts and Applications of Molecular Similarity*, Wiley, New York (1990)). It is used to analyze and categorize chemical phenomena, rationalize the behavior and function of molecules, and design new chemical entities with improved physical, chemical, and biological properties. Molecular similarity is typically quantified in the form of a numerical index derived either through direct observation, or through the measurement of a set of characteristic properties (descriptors), which are subsequently combined in some form of dissimilarity or distance measure. For large collections of compounds, similarities are usually described in the form of a symmetric matrix that contains all the pairwise relationships between the molecules in the collection. Unfortunately, pairwise similarity matrices do not lend themselves for numerical processing and visual inspection. A common solution to this problem is to embed the objects into a low-dimensional Euclidean space in a way that preserves the original pairwise proximities as faithfully as possible. This approach, known as multidimensional scaling (MDS) (Torgeson, W. S., *Psychometrika* 17:401–419 (1952); Kruskal, J. B., *Phychometrika* 29:115–129 (1964)) or nonlinear mapping (NLM) (Sammon, J. W., *IEEE Trans. Comp.* C18:401–409 (1969)), converts the data points into a set of real-valued vectors that can subsequently be used for a variety of pattern recognition and classification tasks.

Given a set of k objects, a symmetric matrix, $r_{ij}$, of relationships between these objects, and a set of images on a m-dimensional map $\{y_i, i=1, 2, \ldots, k; y_i \in \Re^m\}$, the problem is to place $y_i$ onto the map in such a way that their Euclidean distances $d_{ij}=\|y_i-y_j\|$ approximate as closely as possible the corresponding values $r_{ij}$. The quality of the projection is determined using a sum-of-squares error function known as stress, which measures the differences between $d_{ij}$ and $r_{ij}$ over all $k(k-1)/2$ possible pairs. This function is numerically minimized in order to generate the optimal map. This is typically carried out in an iterative fashion by: (1) generating an initial set of coordinates $y_i$, (2) computing the distances $d_{ij}$, (3) finding a new set of coordinates $y_i$ that lead to a reduction in stress using a steepest descent algorithm, and (4) repeating steps (2) and (3) until the change in the stress function falls below some predefined threshold. There is a wide variety of MDS algorithms involving different error (stress) functions and optimization heuristics, which are reviewed in Schiffman, Reynolds and Young, *Introduction to Multidimensional Scaling*, Academic Press, New York (1981); Young and Hamer, *Multidimensional Scaling: History, Theory and Applications*, Erlbaum Associates, Inc., Hillsdale, N.J. (1987); Cox and Cox, *Multidimensional Scaling*, Number 59 in *Monographs in Statistics and Applied Probability*, Chapman-Hall (1994), and Borg, I., Groenen, P., Modem Multidimensional Scaling, Springer-Verlag, New York, (1997). The contents of these publications are incorporated herein by reference in their entireties.

Unfortunately, the quadratic nature of the stress function (i.e. the fact that the computational time required scales proportionally to $k^2$) make these algorithms impractical for data sets containing more than a few thousand items. Several attempts have been devised to reduce the complexity of the task. (See Chang, C. L., and Lee, R. C. T., *IEEE Trans. Syst., Man, Cybern.*, 1973, SMC-3, 197–200; Pykett, C. E., *Electron. Lett.*, 1978, 14, 799–800; Lee, R. C. Y., Slagle, J. R., and Blum, H., *IEEE Trans. Comput.*, 1977, C-27, 288–292; Biswas, G., Jain, A. K., and Dubes, R. C., *IEEE Trans. Pattern Anal. Machine Intell.*, 1981, PAMI-3(6), 701–708). However, these methods either focus on a small subset of objects or a small fraction of distances, and the resulting maps are generally difficult to interpret.

Recently, two very effective alternative strategies were described. The first is based on a self-organizing procedure which repeatedly selects subsets of objects from the set of objects to be mapped, and refines their coordinates so that their distances on the map approximate more closely their corresponding relationships. U.S. Pat. Nos. 6,295,514 and 6,453,246, each of which is incorporated by reference herein in its entirety). The method involves the following steps: (1) placing the objects on the map at some initial coordinates, $y_i$, (2) selecting a subset of objects, (3) revising the coordinates, $y_i$, of at least some of the selected objects so that at least some of their distances, $d_{ij}$, match more closely their corresponding relationships $r_{ij}$, (4) repeating steps (2) and (3) for additional subsets of objects, and (4) exporting the refined coordinates, $y_i$, for the entire set of objects or any subset thereof.

The second method attempts to derive an analytical mapping function that can generate mapping coordinates from a set of object features. (See U.S. application Ser. No. 09/303,671, filed May 3, 1999, and U.S. application Ser. No. 09/814,160, filed Mar. 22, 2001, each of which is incorporated by reference herein in its entirety). The method works as follows. Initially, a subset of objects from the set of objects to be mapped and their associated relationships are selected. This subset of objects is then mapped onto an m-dimensional map using the self-organizing procedure described above, or any other MDS algorithm. Hereafter, the coordinates of objects in this m-dimensional map shall be referred to as "output coordinates" or "output features". In addition, a set of n attributes are determined for each of the selected subset of objects. Hereafter, these n attributes shall be referred to as "input coordinates" or "input features". Thus, each object in the selected subset of objects is associated with an n-dimensional vector of input features and an m-dimensional vector of output features. A supervised machine learning approach is then employed to determine a functional relationship between the n-dimensional input and m-dimensional output vectors, and that functional relationship is recorded. Hereafter, this functional relationship shall be referred to as a "mapping function". Additional objects that are not part of the selected subset of objects may be mapped by computing their input features and using them as input to the mapping function, which produces their output coordinates. The mapping function can be encoded in a neural network or a collection of neural networks.

Both the self-organizing and the neural network methods are general and can be used to produce maps of any desired dimensionality.

MDS can be particularly valuable for analyzing and visualizing combinatorial chemical libraries. A combinatorial library is a collection of chemical compounds derived from the systematic combination of a prescribed set of chemical building blocks according to a specific reaction protocol. A combinatorial library is typically represented as a list of variation sites on a molecular scaffold, each of which is associated with a list of chemical building blocks. Each compound (or product) in a combinatorial library can be represented by a unique tuple, $\{r_1, r_2, \ldots, r_d\}$, where $r_i$ is the building block at the i-th variation site, and d is the number of variation sites in the library. For example, a polypeptide combinatorial library is formed by combining a set of chemical building blocks called amino acids in every possible way for a given compound length (here, the number of variation sites is the number of amino acids along the polypeptide chain). Millions of products theoretically can be synthesized through such combinatorial mixing of building blocks. As one commentator has observed, the systematic combinatorial mixing of 100 interchangeable chemical building blocks results in the theoretical synthesis of 100 million tetrameric compounds or 10 billion pentameric compounds (Gallop et al., "Applications of Combinatorial Technologies to Drug Discovery, Background and Peptide Combinatorial Libraries," J. Med. Chem. 37, 1233–1250 (1994), which is incorporated by reference herein in its entirety). A computer representation of a combinatorial library is often referred to as a virtual combinatorial library.

MDS can simplify the analysis of combinatorial libraries in two important ways: (1) by reducing the number of dimensions that are required to describe the compounds in some abstract chemical property space in a way that preserves the original relationships among the compounds, and (2) by producing Cartesian coordinate vectors from data supplied directly or indirectly in the form of molecular similarities, so that they can be analyzed with conventional statistical and data mining techniques. Typical applications of coordinates obtained with MDS include visualization, diversity analysis, similarity searching, compound classification, structure-activity correlation, etc. (See, e.g., Agrafiotis, D. K., The diversity of chemical libraries, *The Encyclopedia of Computational Chemistry*, Schleyer, P. v. R., Allinger, N. L., Clark, T., Gasteiger, J., Kollman, P. A., Schaefer III, H. F., and Schreiner, P. R., Eds., John Wiley & Sons, Chichester, 742–761 (1998); and Agrafiotis, D. K., Myslik, J. C., and Salemme, F. R., Advances in diversity profiling and combinatorial series design, *Mol. Diversity*, 4(1), 1–22 (1999), each of which is incorporated by reference herein in its entirety).

Analyzing a combinatorial library based on the properties of the products (as opposed to the properties of their building blocks) is often referred to as product-based design. Several product-based methodologies for analyzing virtual combinatorial libraries have been developed. (See, e.g., Sheridan, R. P., and Kearsley, S. K., Using a genetic algorithm to suggest combinatorial libraries, *J. Chem. Info. Comput. Sci*, 35, 310–320 (1995); Weber, L., Wallbaum, S., Broger, C., and Gubemator, K., Optimization of the biological activity of combinatorial compound libraries by a genetic algorithm, *Angew. Chem. Int. Ed. Eng*, 34, 2280–2282 (1995); Singh, J., Ator, M. A., Jaeger, E. P., Allen, M. P., Whipple, D. A., Soloweij, J. E., Chowdhary, S., and Treasurywala, A. M., Application of genetic algorithms to combinatorial synthesis: a computational approach for lead identification and lead optimization, *J. Am. Chem. Soc.*, 118, 1669–1676 (1996); Agrafiotis, D. K., Stochastic algorithms for maximizing molecular diversity, *J. Chem. Info. Comput. Sci.*, 37, 841–851 (1997); Brown, R. D., and Martin, Y. C., Designing combinatorial library mixtures using genetic algorithms, *J. Med. Chem.*, 40, 2304–2313 (1997); Murray, C. W., Clark, D. E., Auton, T. R., Firth, M. A., Li, J., Sykes, R. A., Waszkowycz, B., Westhead, D. R. and Young, S. C., PRO_SELECT: combining structure-based drug design and combinatorial chemistry for rapid lead discovery. 1. Technology, *J. Comput.Aided Mol. Des.*, 11, 193–207 (1997); Agrafiotis, D. K., and Lobanov, V. S., An efficient implementation of distance-based diversity metrics based on k-d trees, *J. Chem. Inf Comput. Sci.*, 39, 51–58 (1999); Gillett, V. J., Willett, P., Bradshaw, J., and Green, D. V. S., Selecting combinatorial libraries to optimize diversity and physical properties, *J. Chem. Info. Comput. Sci.*, 39, 169–177 (1999); Stanton, R. V., Mount, J., and Miller, J. L., Combinatorial library design: maximizing model-fitting compounds with matrix synthesis constraints, *J. Chem. Info. Comput. Sci.*, 40, 701–705 (2000); and Agrafiotis, D. K., and Lobanov, V. S., Ultrafast algorithm for designing focused combinatorial arrays, *J. Chem. Info. Comput. Sci.*, 40, 1030–1038 (2000), each of which is incorporated by reference herein in its entirety).

However, as will be understood by a person skilled in the relevant art(s), this approach requires explicit enumeration (i.e., virtual synthesis) of the products in the virtual library. This process can be prohibitively expensive when the library contains a large number of products. That is, the analysis cannot be accomplished in a reasonable amount of time using available computing systems. In such cases, the most common solution is to restrict attention to a smaller subset of products from the virtual library, or to consider each variation site independently of all the others. (See, e.g., Martin, E. J., Blaney, J. M., Siani, M. A., Spellmeyer, D. C., Wong, A. K., and Moos, W. H., *J. Med Chem.*, 38, 1431–1436 (1995); Martin, E. J., Spellmeyer, D. C., Critchlow, R. E. Jr., and Blaney, J. M., *Reviews in Computational Chemistry*, Vol. 10, Lipkowitz, K. B., and Boyd, D. B., Eds., VCH, Weinheim (1997); and Martin, E., and Wong, A., Sensitivity analysis and other improvements to tailored combinatorial library design, *J. Chem. Info. Comput. Sci.*, 40, 215–220 (2000), each of which is incorporated by reference herein in its entirety). Unfortunately, the latter approach, which is referred to as reagent-based design, often produces inferior results. (See, e.g., Gillet, V. J., Willett, P., and Bradshaw, J., *J. Chem. Inf. Comput. Sci.*; 37(4), 731–740 (1997); and Jamois, E. A., Hassan, M., and Waldman, M., Evaluation of reagent-based and product-based strategies in the design of combinatorial library subsets, *J. Chem. Inf Comput. Sci.*, 40, 63–70 (2000), each of which is incorporated by reference herein in its entirety).

Hence there is a need for methods, systems, and computer program products that can be used to analyze large combinatorial chemical libraries, which do not have the limitations discussed above. In particular, there is a need for methods, systems, and computer program products for rapidly generating mapping coordinates for compounds in a combinatorial library that do not require the enumeration of every possible product in the library.

SUMMARY OF THE INVENTION

The present invention provides a method, system, and computer program product for generating mapping coordinates of combinatorial library products from features of library building blocks.

As described herein, at least one feature is determined for each building block of a combinatorial library having a plurality of products. A training subset of products is selected from the plurality of products in the combinatorial library, and at least one mapping coordinate is determined for each product in the training subset of products. A set of building blocks is identified for each product in the training subset of products, and features associated with these building blocks are combined to form an input features vector for each product in the training subset of products. A supervised machine learning approach is used to infer a mapping function $f$ that transforms the input features vector to the corresponding at least one mapping coordinate for each product in the training subset of products. The mapping function $f$ is encoded in a computer readable medium. After the mapping function $f$ is inferred, it is used for determining, estimating, or generating mapping coordinates of other products in the combinatorial library. Mapping coordinates of other products are determined, estimated, or generated from their corresponding input features vectors using the inferred mapping function $f$. Sets of building blocks are identified for a plurality of additional products in the combinatorial library. Input features vectors are formed for the plurality of additional products. The input features vectors for the plurality of additional products are transformed using the mapping function $f$ to obtain at least one estimated mapping coordinate for each of the plurality of additional products.

In embodiments of the invention, laboratory-measured values and/or computed values are used as features for the building blocks of the combinatorial library. In embodiments of the invention, at least one of the features of the building blocks at a particular variation site in the combinatorial library is the same as at least one of the features of the building blocks at a different variation site in the library. In accordance with the invention, features of building blocks represent reagents used to construct the combinatorial library, fragments of reagents used to construct the combinatorial library, and/or modified fragments of reagents used to construct the combinatorial library. Other features that can be used in accordance with the invention will become apparent to individuals skilled in the relevant arts given the description of the invention herein.

In an embodiment, the mapping function $f$ is implemented using a neural network. The neural network is trained to implement the mapping function using the input features vector and the corresponding at least one mapping coordinate for each product of the training subset of products.

In other embodiments, the mapping function $f$ is a set of specialized mapping functions $f_1$ through $f_n$. In an embodiment, each such specialized mapping function is implemented using a neural network.

In an embodiment, the mapping coordinates for the training subset of products are obtained by generating an initial set of mapping coordinates for the training subset of products and refining the coordinates in an iterative manner. In an embodiment, this is accomplished by selecting two products from the training subset of products and refining the mapping coordinates of at least one of the selected products based on the coordinates of the two products and a distance between the two products. The mapping coordinates of at least one of the selected products are refined so that the distance between the refined coordinates of the two products is more representative of a relationship between the products. This process is typically repeated for additional products of the training subset of products until a stop criterion is satisfied.

In another embodiment, the generation of mapping coordinates for the training subset of products is accomplished by selecting at least three products from the training subset of products and refining the mapping coordinates of at least some of the selected products based on the coordinates of at least some of the selected products and at least some of the distances between the selected products. The mapping coordinates of at least some of the selected products are refined so that at least some of the distances between the refined coordinates of at least some of the selected products are more representative of corresponding relationships between the products. This process is typically repeated for additional subsets of products from the training subset of products until a stop criterion is satisfied.

In other embodiments, the mapping coordinates for the training subset of products are generated using multidimensional scaling or nonlinear mapping so that the distances between the mapping coordinates of the products in the training subset of products are representative of corresponding relationships between the products.

In other embodiments, the mapping coordinates for the training subset of products are obtained from a different mapping function $f^*$. In one embodiment, the mapping function $f^*$ takes as input a set of features associated with each product in the training subset of products and produces the corresponding at least one mapping coordinate for each product in the training subset of products. In another embodiment, the mapping function $f^*$ takes as input a set of features associated with building blocks associated with each product in the training subset of products and produces the corresponding at least one mapping coordinate for each product in the training subset of products.

In other embodiments, the mapping coordinates for the training subset of products are obtained from a computer readable medium.

Further embodiments, features, and advantages of the present invention, as well as the structure and operation of the various embodiments of the present invention, are described in detail below with reference to the accompanying figures.

BRIEF DESCRIPTION OF THE DRAWINGS/FIGURES

The present invention is described with reference to the accompanying drawings wherein:

FIG. 1 illustrates an example combinatorial neural network according to an embodiment of the present invention;

FIGS. 2A–B illustrate a flowchart of a method for generating coordinates for products in a combinatorial library according to an embodiment of the present invention;

FIGS. 3A–B illustrate a flowchart of a second method for generating coordinates for products in a combinatorial library according to an embodiment of the present invention;

DETAILED DESCRIPTION OF THE INVENTION

Figure 1:
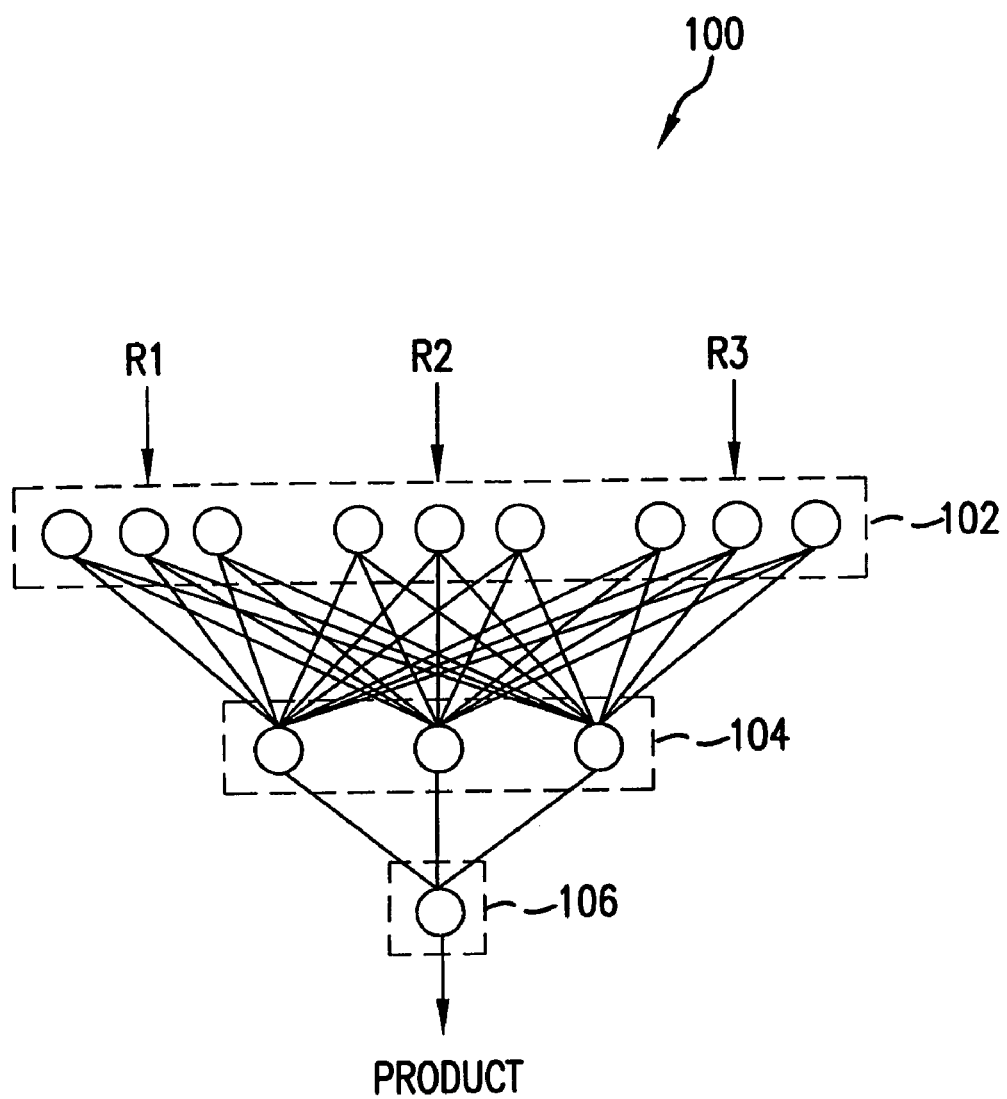

Preferred embodiments of the present invention are now described with references to the figures, where like reference numbers indicate identical or functionally similar elements. Also in the figures, the left most digit(s) of each reference number corresponds to the figure in which the reference number is first used. While specific configurations and arrangements are discussed, it should be understood that this is done for illustrative purposes only. One skilled in the relevant art will recognize that other configurations and arrangements can be used without departing from the spirit and scope of the invention. It will also be apparent to one skilled in the relevant art(s) that this invention can also be employed in a variety of other devices and applications, and is not limited to just the embodiments described herein.

1. Overview of the Invention

The present invention provides a method, system, and computer program product for generating mapping coordinates of combinatorial library products from features of library building blocks. In operation, features of library building blocks and mapping coordinates for a training subset of products in the combinatorial library are obtained and used to infer a mapping function $f$ that transforms building block features to mapping coordinates for each product in the training subset of products. The mapping function $f$ is encoded in a computer readable medium.

The mapping function $f$ can be retrieved and used to generate mapping coordinates for additional products in the combinatorial library from features of building blocks associated with the additional products. In an embodiment, after the mapping function $f$ is inferred, mapping coordinates of additional products in the combinatorial library are generated by obtaining features of the building blocks and using them as input to the mapping function $f$, which generates mapping coordinates for the additional library products. The mapping coordinates can then be used for any subsequent analysis, searching, or classification. As will be understood by a person skilled in the relevant art, given the description herein, the present invention can be applied to a wide variety of mapping coordinates and/or building block features.

2. Combinatorial Neural Networks

As described below, in some embodiments of the invention the mapping function $f$ is implemented using a neural network. This neural network is hereafter referred to as a combinatorial network or combinatorial neural network. The combinatorial network is trained to generate at least one mapping coordinate of the combinatorial library products from input features of their respective building blocks. As used herein, the term "mapping coordinates" refers to the mapping coordinates of the library products, and the term "building block features" refers to the input features of the library building blocks (e.g., reagents, fragments of reagents, and/or modified fragments of reagents).

Generally speaking, a combinatorial network comprises an input layer containing $n_1+n_2+\ldots+n_r$ neurons, where $r$ is the number of variation sites in the combinatorial library and $n_i$ is the number of input features of the building blocks at the i-th variation site. In addition, a combinatorial network comprises one or more hidden layers containing one or more neurons each, and an output layer having a single neuron for each mapping coordinate generated by the neural network.

FIG. 1 illustrates an example combinatorial network 100 according to an embodiment of the invention. Combinatorial network 100 is a fully connected multilayer perceptron (MLP). In accordance with the invention, the outputs of combinatorial network 100 represent mapping coordinates of the library products.

As illustrated in FIG. 1, combinatorial network 100 has an input layer 102, a hidden layer 104, and an output layer 106. In an embodiment, a nonlinear transfer function, such as the logistic transfer function $f(x)=1/(1+e^{-x})$, is used for the hidden and/or output layers. Combinatorial network 100 can be trained in accordance with the invention using, for example, the error back-propagation algorithm (see, e.g., S. Haykin, Neural Networks, Macmillan, New York (1994), which is incorporated by reference herein in its entirety). Other neural network architectures and/or training algorithms that can be used in accordance with the invention will become apparent to individuals skilled in the relevant arts given the description of the invention herein.

As will be understood by persons skilled in the relevant art given the description herein, training data used to train a combinatorial network typically include two sets of parameters. The first set consists of one or more input features for each of the library building blocks. The second set consists of one or more mapping coordinates for the training subset of products. The building block features are concatenated into a single array, and are presented to the network in the same order (e.g., $f_{11}, f_{12}, \ldots, f_{1n1}, f_{21}, f_{22}, \ldots, f_{2n2}, \ldots, f_{r1}, f_{r2}, \ldots, f_{mr}$, where $f_{ij}$ is the j-th feature of the building block at the i-th variation site).

In an embodiment, the training subset of products presented to a network is determined by random sampling. (See Agrafiotis, D. K., and Lobanov, V. S., Nonlinear Mapping Networks. *J. Chem. Info. Comput. Sci.*, 40, 1356–1362 (2000), which is incorporated by reference herein in its entirety).

3. Method Embodiments of the Invention

As described herein, the invention permits the in silico characterization and analysis of large virtual combinatorial libraries. A virtual combinatorial library is an electronic representation of a collection of chemical compounds or "products" generated by the systematic combination of a number of chemical "building blocks" such as reagents according to a specific reaction protocol. Typically, embodiments of the invention are significantly faster than conventional library analysis methodologies that are based on full enumeration of the combinatorial products.

A. Example Method 200

Figure 2A:
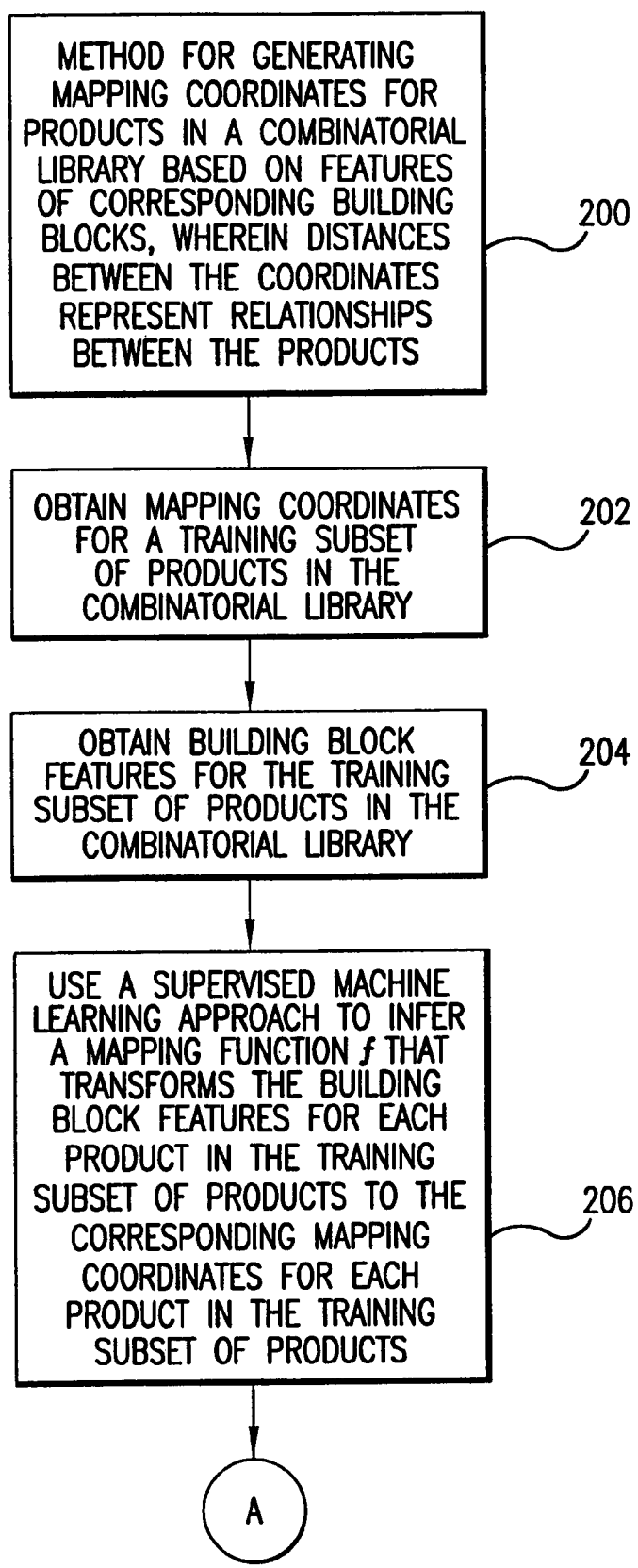
Figure 2B:
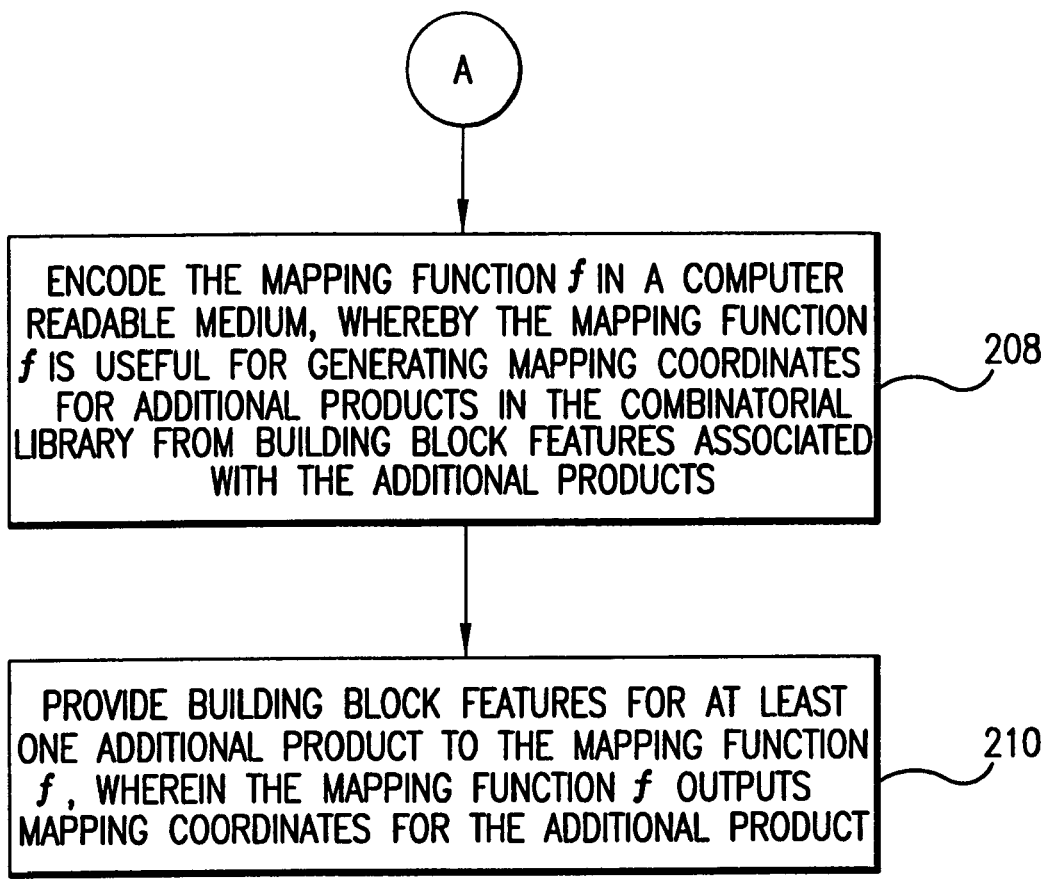

FIGS. 2A and 2B illustrate a flowchart of the steps of a method 200 for generating mapping coordinates of products in a virtual combinatorial library based on features of corresponding building blocks. Typically, distances between the mapping coordinates of products represent relationships between the products.

The steps of method 200 will now be described with reference to FIGS. 2A and 2B. Method 200 begins with step 202.

In step 202, mapping coordinates are obtained for a training subset of products in the virtual combinatorial library.

In an embodiment of the invention, a training subset of products from the virtual combinatorial library is identified in step 202. Relationships between products in the training subset of products are then obtained and are used to produce mapping coordinates for the products in the training subset of products.

In an embodiment, distances between mapping coordinates of the products in the training subset of products are representative of corresponding relationships between the products.

In other embodiments, mapping coordinates for the products in the training subset of products are obtained in step 202 by generating an initial set of mapping coordinates for the products in the training subset of products and refining the coordinates in an iterative manner until a stop criterion is satisfied. This may be accomplished, for example, by selecting two products at a time from the training subset of products and refining the mapping coordinates of at least one of the selected products based on the coordinates of the two products and a distance between the two products. The mapping coordinates of at least one of the selected products is refined so that the distance between the refined coordinates of the two products is more representative of a relationship between the products. This mapping process is further described in U.S. Pat. Nos. 6,295,514 and 6,453,246.

In other embodiments, the generation of mapping coordinates for the products in the training subset of products is accomplished by selecting at least three products from the training subset of products and refining the mapping coordinates of at least some of the selected products based on the coordinates of at least some of the selected products and at least some of the distances between the selected products. The mapping coordinates of at least some of the selected products are refined so that at least some of the distances between the refined coordinates of at least some of the selected products are more representative of corresponding relationships between the products. This process is typically repeated for additional subsets of products from the training subset of products until a stop criterion is satisfied. This mapping process is further described in U.S. Pat. Nos. 6,295,514 and 6,453,246.

In other embodiments, the mapping coordinates for the training subset of products are generated using multidimensional scaling or nonlinear mapping so that the distances between the mapping coordinates of the products in the training subset of products are representative of corresponding relationships between the products.

In other embodiments, the mapping coordinates for the training subset of products are obtained from a different mapping function $f^*$. In one embodiment, the mapping function $f^*$ takes as input a set of features associated with each product in the training subset of products and produces the corresponding at least one mapping coordinate for each product in the training subset of products. In another embodiment, the mapping function $f^*$ takes as input a set of features associated with building blocks associated with each product in the training subset of products and produces the corresponding at least one mapping coordinate for each product in the training subset of products.

In an embodiment, relationships between products in the training subset of products are obtained by obtaining a set of properties for each product in the training subset of products, and computing relationships between products using the properties of the training subset of products. As will be understood by persons skilled in the relevant art, any relationship measure that can relate products in the training subset of products can be used in this regard. In an embodiment, relationships between products represent similarities or dissimilarities between the products.

In other embodiments, mapping coordinates for the products in the training subset of products are obtained by obtaining a set of properties for each product in the training subset of products, and computing a set of latent coordinates from at least some of the properties of the training subset of products using a dimensionality reduction method.

In other embodiments, the mapping coordinates for the training subset of products are obtained in step 202, for example, by retrieving the mapping coordinates from a computer readable medium.

Other means that can be used in accordance with the invention to obtain mapping coordinates for the training subset of products will become apparent to individuals skilled in the relevant arts given the description of the invention herein.

In step 204, building block features (i.e., numerical representations of the building blocks of the combinatorial library) are obtained for the training subset of products. These building block features can be obtained in any desired manner. Furthermore, there is no requirement in step 204 to obtain the same type of numerical representations for the library building blocks as those obtained in step 202 for the training subset of products.

In embodiments of the invention, laboratory-measured values and/or computed values are used as features for the building blocks of the combinatorial library. In embodiments of the invention, at least one of the features of the building blocks at a particular variation site in the combinatorial library is the same as at least one of the features of the building blocks at a different variation site in the library.

In accordance with the invention, features of building blocks represent reagents used to construct the combinatorial library, fragments of reagents used to construct the combinatorial library, and/or modified fragments of reagents used to construct the combinatorial library. Other features that can be used in accordance with the invention will become apparent to individuals skilled in the relevant arts given the description of the invention herein.

In step 206, a supervised machine learning approach is used to infer a mapping function $f$ that transforms the building block features for each product in the training subset of products to the corresponding mapping coordinates for each product in the training subset of products. In embodiments of the invention, step 206 involves training a combinatorial neural network to transform the building block features for each product in the training subset of products to the corresponding mapping coordinates for each product in the training subset of products.

In step 208, the mapping function $f$ is encoded in a computer readable medium, whereby the mapping function $f$ is useful for generating mapping coordinates for additional products in the combinatorial library from building block features associated with the additional products. In one embodiment of the invention, the mapping function $f$ is implemented in step 208 using a neural network. In other embodiments, the mapping function $f$ is implemented in step 208 using a set of specialized mapping functions $f_1$ through $f_n$. In some embodiments, each such specialized mapping function is implemented using a neural network. Other methods can also be used to implement the mapping function $f$. In embodiments of the invention, step 208 is performed in conjunction with step 206.

It accordance with the invention, the encoded mapping function $f$ may be distributed and used by individuals to analyze virtual combinatorial libraries. In embodiments, the encoded mapping function $f$ is distributed as a part of a computer program product. These computer program products can be used to perform optional step 210.

In optional step 210, building blocks features for at least one additional product in the combinatorial library are provided to the mapping function $f$, wherein the mapping function $f$ outputs mapping coordinates for the additional product. The mapping coordinates produced by the mapping function $f$ can be used, for example, to analyze, search, or classify additional products in the combinatorial library. When performed, optional step 210 can be performed by the same person or legal entity that performed steps 202–208, or by a different person or entity.

B. Example Method 300

Figure 3A:
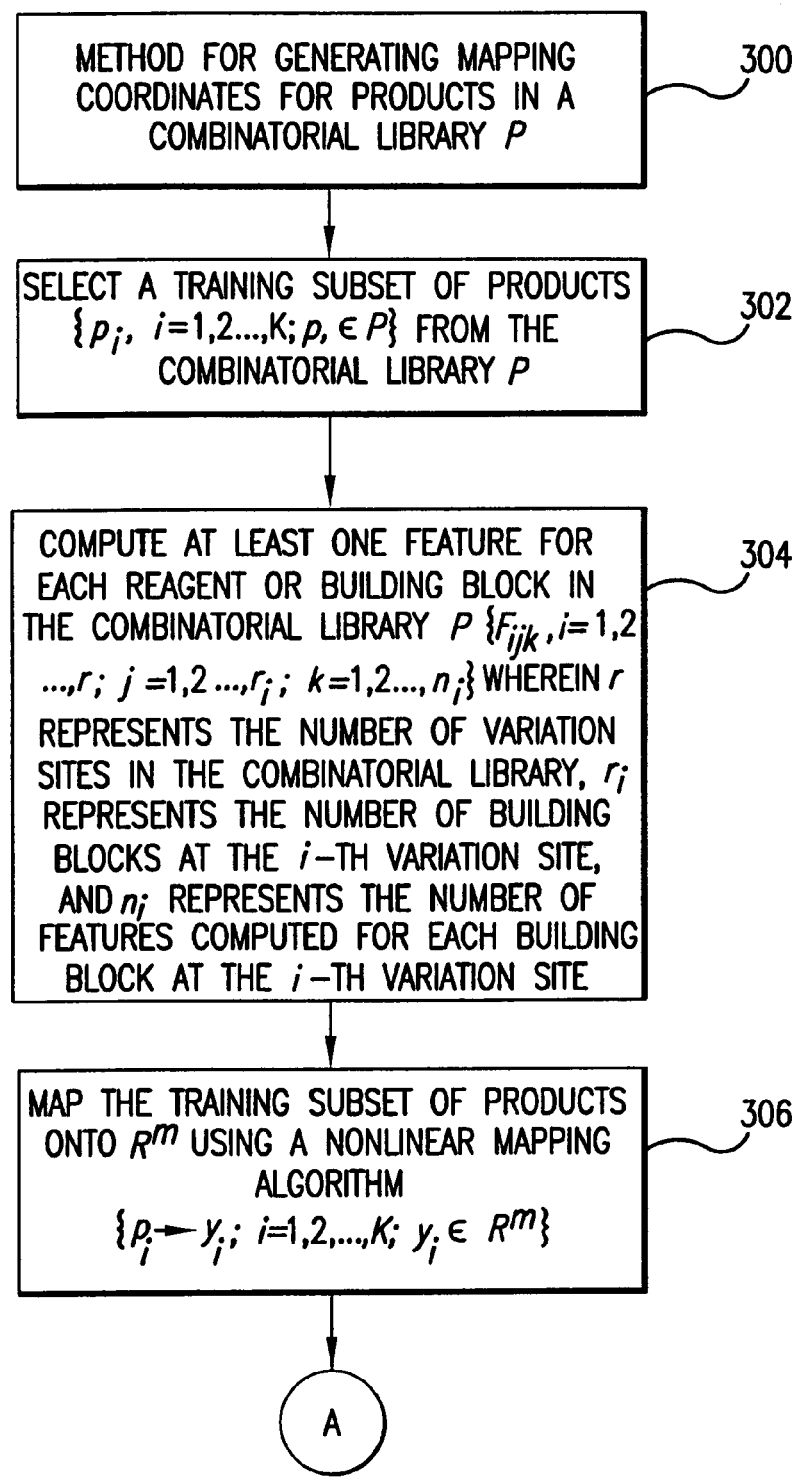
Figure 3B:
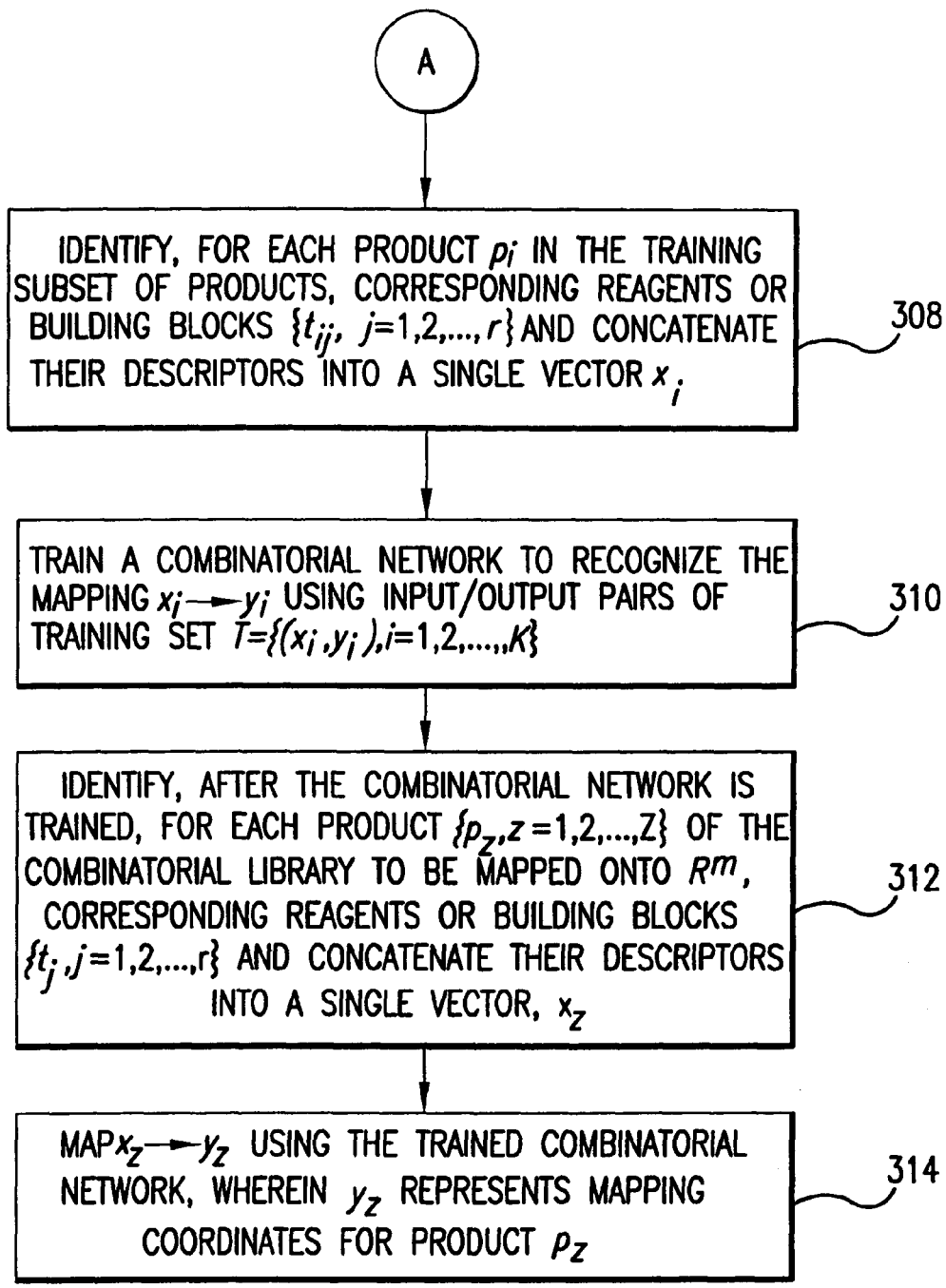

FIGS. 3A and 3B illustrate a flowchart of the steps of a second method 300 for generating coordinates for products in a virtual combinatorial library according to an embodiment of the invention. As will become apparent from the description, method 300 includes a combinatorial network training phase (steps 302, 304, 306, 308, and 310) and an optional product mapping coordinate generation phase (steps 312 and 314). The steps of method 300 will now be described with reference to FIGS. 3A and 3B.

In step 302 of method 300, a subset of training products $\{p_i, i=1, 2, \ldots, k; p_i \in P\}$ is selected from a combinatorial library P.

The training subset of products $\{p_i, i=1, 2, \ldots, k; p_i \in P\}$ selected in step 302 can be chosen in any manner. For example, the training subset can be chosen randomly or non-randomly. In most cases, the composition of a particular training subset does not have a significant influence on the quality of a map as long as it is representative of the combinatorial library from which it is selected. Empirical evidence suggests that for moderately large combinatorial libraries (~$10^5$ products), a training subset on the order of 1–3% is usually sufficient to train a combinatorial network according to the invention.

In step 304 of method 300, features of choice are computed for each reagent or building block in the combinatorial library P, $\{f_{ijk}, i=1, 2, \ldots, r; j=1, 2, \ldots, r_i; k=1, 2, \ldots, n_i\}$, where r is the number of variation sites in the combinatorial library, $r_i$ is the number of building blocks at the i-th variation site, and $n_i$ is the number of features used to characterize each building block at the i-th variation site. At least one feature is computed for each reagent or building block. Features computed for the reagents or building blocks at a particular variation site in the combinatorial library may not be the same as features computed for the building blocks at different variation sites in the combinatorial library. In embodiments of the invention, at least some of the reagent or building block features represent latent variables derived from other reagent or building block data, such as principal components, principal factors, MDS coordinates, etc.

In step 306, the training subset of products selected in step 302 is mapped onto $\Re^m$ using a nonlinear mapping algorithm ($p_i \to y_i$, i=1, 2, \ldots, k, $y_i \in \Re^m$) and a function of choice for assigning relationships between products. This function takes as input a pair of products or data associated with a pair of products and returns a numerical value that represents a relationship (similarity, dissimilarity, or some other type of relationship) between the products.

In embodiments of the invention, the nonlinear mapping algorithm ($p_i \to y_i$, i=1, 2, \ldots, k, $y_i \in \Re^m$ is any conventional multidimensional scaling or nonlinear mapping algorithm. In other embodiments, the nonlinear mapping algorithm ($p_i \to y_i$, i=1, 2, \ldots, k, $y_i \in \Re^m$ comprises the following steps to determine each $y_i$: (1) placing the training subset of products on an m-dimensional map at some initial coordinates; (2) selecting a pair of products from the training subset of products having a known or assigned relationship; (3) revising the mapping coordinates of one or both of the selected products based on their assigned relationship and the corresponding distance between the products on the map so that the distance between the products on the m-dimensional map are more representative of the assigned relationship between the products; and (4) repeating steps (2) and (3) for additional pairs of products from the training subset of products until a stop criterion is satisfied. This mapping process is further described in U.S. Pat. Nos. 6,295,514 and 6,453,246.

In other embodiments of the invention, the nonlinear mapping algorithm ($p_i \to y_i$, i=1, 2, \ldots, k, $y_i \in \Re^m$ comprises the following steps to determine each $y_i$: (1) placing the training subset of products on an in-dimensional map at some initial coordinates; (2) selecting at least three products having at least some known or assigned relationships; (3) revising mapping coordinates of at least some of the selected products so that at least some of the distances between the refined coordinates of at least some of the selected products are more representative of corresponding relationships between the products; and (4) repeating steps (2) and (3) for additional subsets of products from the training subset of products until a stop criterion is satisfied. This mapping process is further described in U.S. Pat. Nos. 6,295,514 and 6,453,246.

In step 308 of method 300, for each product $p_i$ of the training subset of products, the corresponding reagents or building blocks $\{t_{ij}, j=1, 2, \ldots, r\}$ of product $p_i$ are identified and their features $f_{t_{ij}1}, f_{t_{ij}2}, \ldots, f_{t_{ij}n_1}, \ldots, f_{t_{ij}n_r}$ are concatenated into a single vector, $x_i$. A training set $T=\{(x_i, y_i), i=1, 2, \ldots, k\}$ is typically denoted.

In step 310, a combinatorial network is trained to reproduce the mapping $x_i \to y_i$ using the input/output pairs of the training set T. In embodiments of the invention, the combinatorial network and its associated parameters can be exported for use by other systems and/or computer program products.

Step 310 ends when the combinatorial network is trained. Once the network is trained, the network can be used to generate mapping coordinates for products of combinatorial library P in accordance with steps 312 and 314 of method 300.

In step 312, for each product $\{p_z, Z=1, 2, \ldots w\}$ of the combinatorial library P to be mapped onto $\Re^m$, corresponding reagents or building blocks $\{t_j, j=1, 2, \ldots, r\}$ are identified, and their features $f_{t_{ij}1}, f_{t_{ij}2}, \ldots, f_{t_{ij}n_1}, \ldots, f_{t_{ij}n_r}$ are concatenated into a single vector, $x_z$. The features of step 312 are the features computed in step 304.

In step 314, the trained combinatorial network is used to map $x_z \to y_z$, wherein $y_z$ represents mapping coordinates for product $p_z$.

In embodiments of the invention, the mapping coordinates produced by the combinatorial network are stored for subsequent retrieval and analysis. The mapping coordinates can be analyzed, for example, using conventional statistical and/or data mining techniques. The mapping coordinates of the products can also be used, for example, to generate a similarity plot of the products for viewing on a display screen. Other methods for analyzing the mapping coordinates of the products will be known to a person skilled in the relevant art given the description herein.

4. Exemplary Applications of the Invention

In this section, two exemplary applications of the present invention are presented. Both of these applications illustrate the generation of 2-dimensional mapping coordinates for the products of a combinatorial library given a set of computed descriptors (properties) of the library products and a molecular similarity function evaluated on the basis of these descriptors. The objective was to map the products in the combinatorial library onto a 2-dimensional map in such a way that the Euclidean distances of the products on the 2-dimensional map approximated as closely as possible the corresponding dissimilarities of the respective products. Thus, the computed dissimilarities of the products were used as a measure of the relationships between the products. The two exemplary applications differ in the function that was used to measure the dissimilarity between two products in the virtual library.

Figure 4:
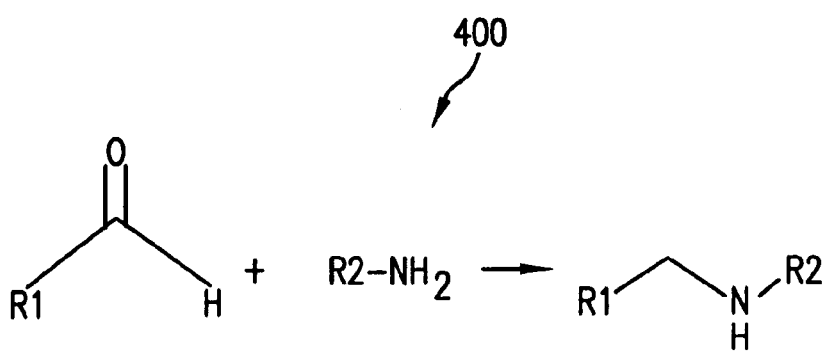
FIG. 4 illustrates a reaction scheme for a reductive amination combinatorial library.

FIG. 4 illustrates the reductive amination reaction scheme 400 that was used to generate the combinatorial library used in the exemplary applications. In accordance with reaction scheme 400, a virtual library of 90,000 products was generated using a set of 300 primary amines and 300 aldehydes. A set of 300 primary amines and 300 aldehydes (i.e., 600 reagents or building blocks) were selected from the Available Chemicals Directory (a database of commercially available reagents marketed by MDL Information Systems, Inc., 140 Catalina Street, San Leandro, Calif. 94577, which is incorporated by reference herein in its entirety) and used in accordance with reaction scheme 400 to generate a library of 90,000 products.

Each of the 600 reagents and 90,000 products was described by two sets of descriptors: (1) Kier-Hall topological indices (KH), and (2) ISIS keys (IK). The former is a collection of 117 molecular connectivity indices, kappa shape indices, subgraph counts, information-theoretic indices, Bonchev-Trinajstićindices, and topological state indices. The latter are 166-dimensional binary vectors, where each bit encodes the presence or absence of a particular structural feature in the molecule. The bit assignment is based on the fragment dictionary used in the ISIS chemical database management system.

To eliminate redundancy in the data, the Kier-Hall (KH) descriptors for the reagents and products were independently normalized and decorrelated using principal component analysis (PCA). This process resulted in an orthogonal set of 24 and 23 latent variables for the reagents and products, respectively, which accounted for 99% of the total variance in the respective data. To simplify the input to the neural networks, PCA was also applied to the binary ISIS keys, resulting in 66 and 70 principal components for the reagents and products, respectively.

In the case of the KH descriptors, the dissimilarity between two products was measured using the Euclidean distance in the 23-dimensional space formed by the products principal components. For the ISIS keys, the dissimilarity between two products was measured using the Tanimoto distance:

$$S = 1 - T$$

where T is the Tanimoto coefficient:

$$T = \frac{|AND(x, y)|}{|IOR(x, y)|}$$

and where x and y represent two binary encoded molecules, AND is the bitwise "and" operation (a bit in the result is set if both of the corresponding bits in the two operands are set), and IOR is the bitwise "inclusive or" operation (a bit in the result is set if either or both of the corresponding bits in the two operands are set).

Figure 5A:
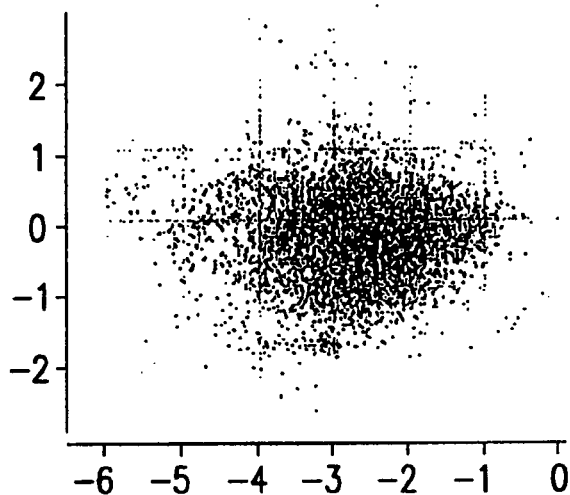
FIG. 5A illustrates an example two-dimensional nonlinear map for a reductive amination library using Kier-Hall descriptors obtained by a non-linear mapping method.
Figure 6A:
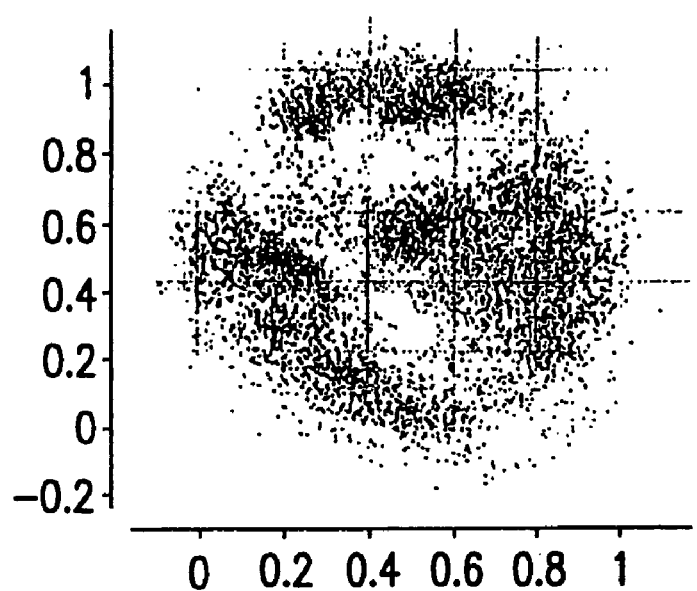
FIG. 6A illustrates an example two-dimensional nonlinear map for a reductive amination library using Isis Keys descriptors obtained by a non-linear mapping method.

In the exemplary applications described herein, the training set was determined by random sampling. Thus, the analysis consisted of the following steps. First, a set of descriptors were computed for each of the reagents that make up the virtual library. A random sample of 3,000 products (the training subset of products) from the virtual library was then identified, and mapped to two dimensions using the pairwise refinement method described above. This method starts by assigning initial mapping coordinates to the training subset of products, and then repeatedly selects two products from the training subset of products and refines their coordinates on the map so that the distance between the coordinates on the map corresponds more closely to the relationship (dissimilarity) between the selected products. This process terminates when a stop criterion is satisfied. The resulting coordinates were used as input to a combinatorial network, which was trained to reproduce the mapping coordinates of the products in the training subset of products from the descriptors of their respective building blocks. Once trained, the neural network was used in a feed-forward manner to map the remaining products in the virtual library. For comparison, the map derived by applying the pairwise refinement process on the entire virtual library was also obtained. These reference maps are shown in FIG. 5A and 6A for the KH and IK descriptors, respectively.

The results discussed herein were obtained using three-layer, fully connected neural networks according to the invention. The neural networks were trained using a standard error back-propagation algorithm (see, e.g., S. Haykin, Neural Networks, Macmillan, New York (1994)). The logistic transfer function $f(x)=1/(1+e^{-e})$ was used for both hidden and output layers. Each network had 10 hidden units and was trained for 500 epochs, using a linearly decreasing learning rate from 1.0 to 0.01 and a momentum of 0.8. During each epoch, the training patterns were presented to the network in a randomized order.

For the KH maps, the input to the neural network consisted of the reagent principal components that accounted for 99% of the total variance in the reagent KH descriptors. For the IK maps, the input to the neural network consisted of the reagent principal components that accounted for 99% of the total variance in the reagent IK binary descriptors.

Figure 5B:
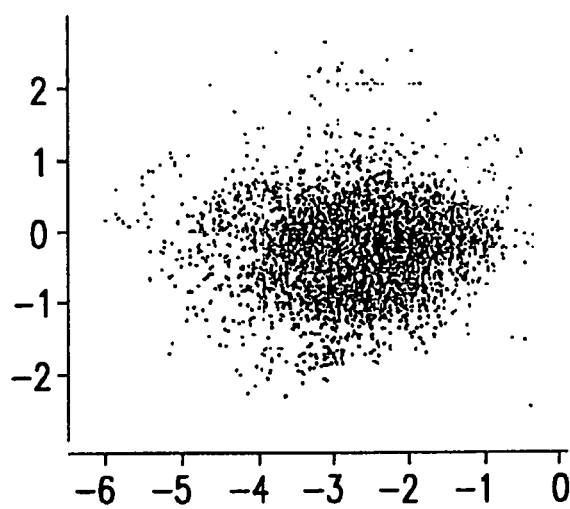
FIG. 5B illustrates an example two-dimensional nonlinear map for a reductive amination library using Kier-Hall descriptors obtained by a combinatorial neural network according to the present invention.
Figure 6B:
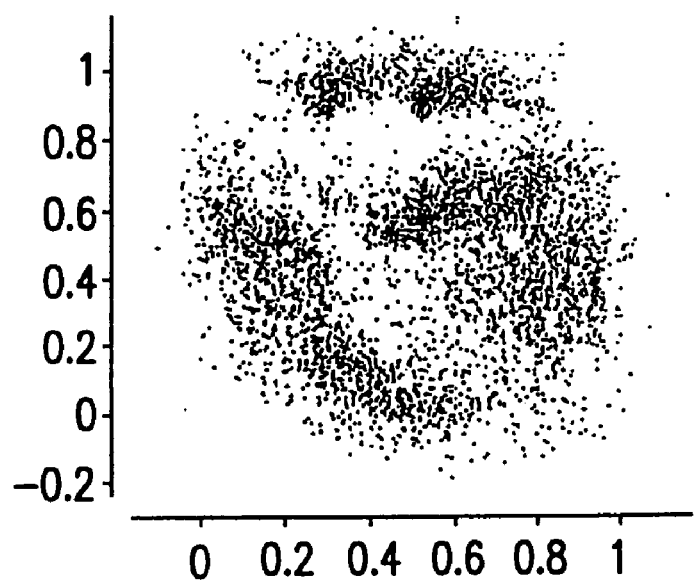
FIG. 6B illustrates an example two-dimensional nonlinear map for a reductive amination library using Isis Keys descriptors obtained by a combinatorial neural network according to the present invention.

The maps obtained with the combinatorial networks trained using the aforementioned procedure are illustrated in FIG. 5B and 6B for the KH and IK descriptors, respectively. As illustrated in FIGS. 5A–B and 6A–B, in both cases, combinatorial networks trained according to the invention produced maps that were comparable to those derived by fully enumerating the entire combinatorial library (FIG. 5A and 6A, respectively). A more detailed study of the effects of network topology and training parameters, sample size, sample composition, structure representation, input and output dimensionality, and combinatorial complexity is described in (Agrafiotis, D. K., and Lobanov, V. S., Multi-dimensional Scaling of Combinatorial Libraries without Explicit Enumeration, *J. Comput. Chem.*, 22, 1712–1722 (2001)), which is incorporated herein by reference in its entirety.

Although the preceding examples focus on 2-dimensional projections, the invention can also be used for mapping products into higher dimensions in order to facilitate their analysis by established statistical methods. Martin et al, for example, has used this technique to convert binary molecular fingerprints into Cartesian vectors so that they could be used for reagent selection using D-optimal experimental design (See, e.g., Martin, E., and Wong, A., Sensitivity analysis and other improvements to tailored combinatorial library design. J. Chem. Info. Comput. Sci., 40, 215–220 (2000), which is incorporated by reference herein in its entirety).

5. System and Computer Program Product Embodiments

Figure 7:
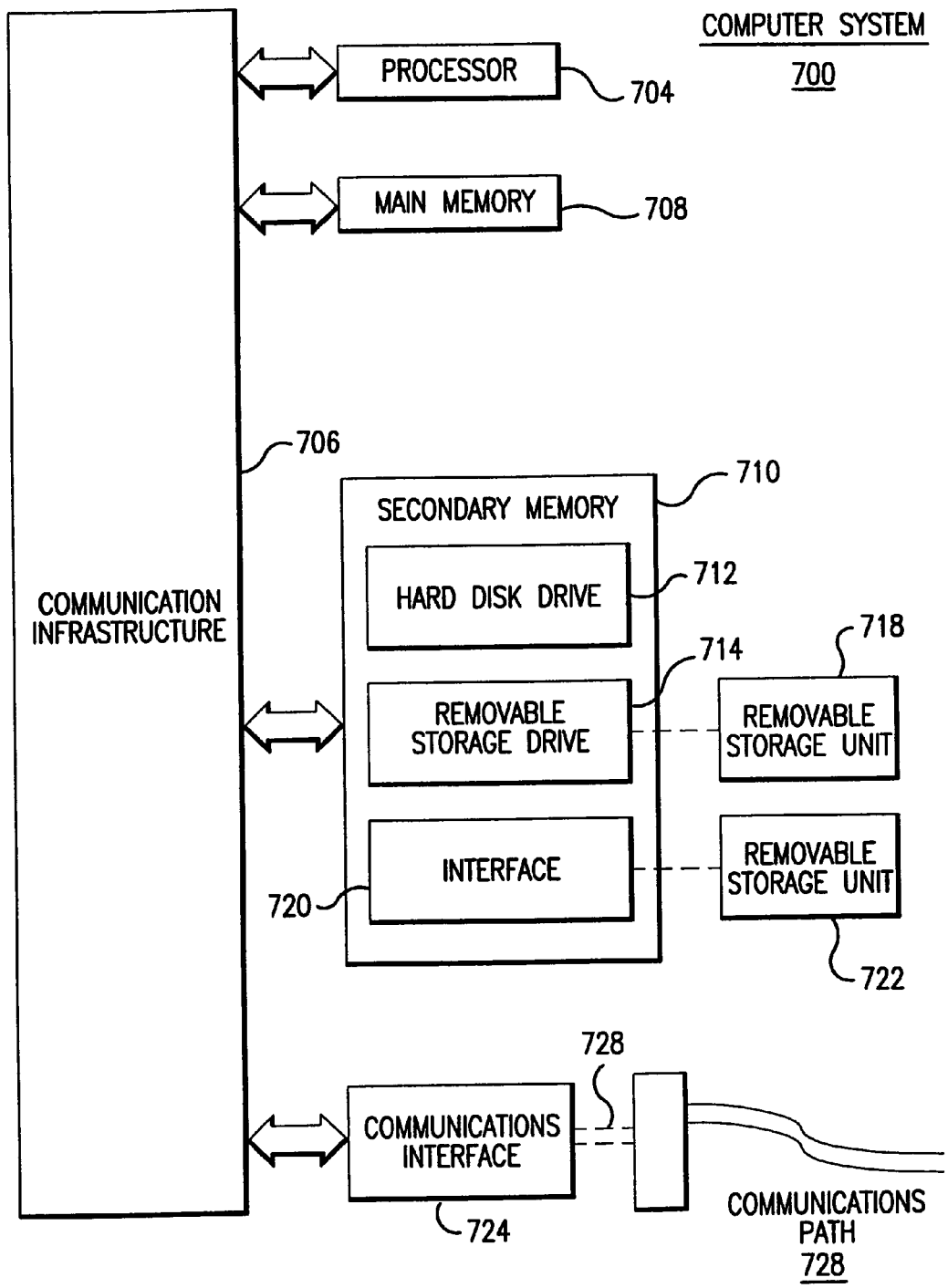
FIG. 7 illustrates an exemplary computing environment within which the invention can operate.

As will be understood by a person skilled in the relevant arts given the description herein, the method embodiments of the invention described above can be implemented as a system and/or a computer program product. FIG. 7 shows an example computer system 700 that supports implementation of the present invention. The present invention may be implemented using hardware, software, firmware, or a combination thereof. It may be implemented in a computer system or other processing system. The computer system 700 includes one or more processors, such as processor 704. The processor 704 is connected to a communication infrastructure 706 (e.g., a bus or network). Various software embodiments can be described in terms of this exemplary computer system. After reading this description, it will become apparent to a person skilled in the relevant art how to implement the invention using other computer systems and/or computer architectures.

Computer system 700 also includes a main memory 708, preferably random access memory (RAM), and may also include a secondary memory 710. The secondary memory 710 may include, for example, a hard disk drive 712 and/or a removable storage drive 714, representing a floppy disk drive, a magnetic tape drive, an optical disk drive, etc. The removable storage drive 714 reads from and/or writes to a removable storage unit 718 in a well-known manner. Removable storage unit 718 represents a floppy disk, magnetic tape, optical disk, etc. As will be appreciated, the removable storage unit 718 includes a computer usable storage medium having stored therein computer software and/or data. In an embodiment of the invention, removable storage unit 718 can contain input data to be projected.

Secondary memory 710 can also include other similar means for allowing computer programs or input data to be loaded into computer system 700. Such means may include, for example, a removable storage unit 722 and an interface 720. Examples of such may include a program cartridge and cartridge interface (such as that found in video game devices), a removable memory chip (such as an EPROM, or PROM) and associated socket, and other removable storage units 722 and interfaces 720, which allow software and data to be transferred from the removable storage unit 722 to computer system 700.

Computer system 700 may also include a communications interface 724. Communications interface 724 allows software and data to be transferred between computer system 700 and external devices. Examples of communications interface 724 may include a modem, a network interface (such as an Ethernet card), a communications port, a PCM-CIA slot and card, etc. Software and data transferred via communications interface 724 are in the form of signals 728 which may be electronic, electromagnetic, optical or other signals capable of being received by communications interface 724. These signals 728 are provided to communications interface 724 via a communications path (i.e., channel) 726. This channel 726 carries signals 728 and may be implemented using wire or cable, fiber optics, a phone line, a cellular phone link, an RF link and other communications channels. In an embodiment of the invention, signals 728 can include input data to be projected.

Computer programs (also called computer control logic) are stored in main memory 708 and/or secondary memory 710. Computer programs may also be received via communications interface 724. Such computer programs, when executed, enable the computer system 700 to perform the features of the present invention as discussed herein. In particular, the computer programs, when executed, enable the processor 704 to perform the features of the present invention. Accordingly, such computer programs represent controllers of the computer system 700.

6. Conclusion

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments, but should be defined only in accordance with the following claims and their equivalents.

What is claimed is:

1. A method for generating coordinates for products in a combinatorial library based on features of corresponding building blocks, the method comprising the steps of:
   (1) obtaining mapping coordinates for a subset of products in the combinatorial library, wherein distances between the mapping coordinates represent relationships between the products;
   (2) obtaining building block features for the subset of products in the combinatorial library;
   (3) using a supervised machine learning approach to infer a mapping function $f$ that transforms the building block features for each product in the subset of products to a corresponding mapping coordinate for each building block feature of each product in the subset of products; and
   (4) encoding the mapping function $f$ in a computer readable medium, whereby the mapping function $f$ is used to generate coordinates corresponding to additional products in the combinatorial library from building block features associated with the additional products.

2. The method according to claim 1, further comprising the step of:
   (5) providing building block features for at least one additional product to the mapping function $f$ wherein the mapping function $f$ outputs generated mapping coordinates for the additional product.

3. The method according to claim 1, wherein step (1) comprises generating the mapping coordinates for the subset of products.

4. The method according to claim 3, wherein step (1) further comprises the steps of:
(a) generating an initial set of mapping coordinates for the subset of products;
(b) selecting two products from the subset of products;
(c) determining a relationship between the two products;
(d) refining the initial set of mapping coordinates of one product selected in step (1)(b) based on the relationship and the corresponding distance between the products on the nonlinear map; and
(e) repeating steps (1)(b) and (1)(c) for additional products until a stop criterion is obtained.

5. The method according to claim 1, wherein step (1) comprises calculating the mapping coordinates for the subset of products using a dimensionality reduction algorithm.

6. The method according to claim 1, wherein step (1) comprises retrieving the mapping coordinates for the subset of products from a computer readable medium.

7. The method according to claim 1, wherein step (2) comprises the step of:
using a laboratory measured value as a feature for each building block in at least one variation site in the combinatorial library.

8. The method according to claim 1, wherein step (2) comprises the step of:
using a computed value as a feature for each building block in at least one variation site in the combinatorial library.

9. The method according to claim 1, wherein at least some of the building block features represent reagents used to construct the combinatorial library.

10. The method according to claim 1, wherein at least some of the building block features represent chemical fragments of reagents used to construct the combinatorial library.

11. The method according to claim 1, wherein at least some of the building block features represent modified chemical fragments of reagents used to construct the combinatorial library.

12. The method according to claim 1, wherein the mapping function $f$ is encoded as a neural network.

13. The method according to claim 1, wherein the mapping function $f$ is a set of mapping functions $f_1$ through $f_n$, each encoded as a neural network.

14. The method of claim 1, wherein step (3) comprises:
(a) placing the selected training subset of products on an m-dimensional nonlinear map using randomly assigned coordinates;
(b) selecting a pair of the products having a similarity relationship;
(c) revising the coordinates of at least one of the selected pair of products based on the similarity relationship and the corresponding distance between the products on the nonlinear map; and
(d) repeating steps (b) and (c) for additional pairs of the products until the distances between the products on the m dimensional nonlinear map are representative of the similarity relationships between the products.

15. A computer program product for generating coordinates for products in a combinatorial library based on features of corresponding building blocks, said computer program product comprising a computer useable medium having computer program logic recorded thereon for controlling a processor, said computer program logic comprising:
a procedure that enables said processor to obtain mapping coordinates for a subset of products in the combinatorial library, wherein distances between the mapping coordinates represent similarity/dissimilarity of the products;
a procedure that enables said processor to obtain building block features for the subset of products in the combinatorial library;
a procedure that enables said processor to use a supervised machine learning approach to infer a mapping function $f$ that transforms the building block features for each product in the subset of products to a corresponding mapping coordinate for each building block feature of each product in the subset of products; and
a procedure that enables said processor to encode the mapping function $f$ in a computer readable medium, whereby the mapping function $f$ is used to generate coordinates corresponding to additional products in the combinatorial library from building block features associated with the additional products.

16. The computer program product of claim 15, further comprising:
a procedure that enable said processor to provide building blocks features for at least one additional product to the mapping function $f$ wherein the mapping function $f$ outputs generated mapping coordinates for the additional product.

17. The computer program product of claim 15, wherein said procedure that enables said processor to obtain mapping coordinates comprises:
a procedure that enables said processor to generate an initial set of mapping coordinates for the subset of products;
a procedure that enables said processor to select two products from the subset of products;
a procedure that enables said processor to determine a relationship between the two products;
a procedure that enable said processor to refine the initial set of mapping coordinates of at least one product selected based on the relationship and the corresponding distance between the products on the nonlinear map; and
a procedure that enables said processor to continue selecting two products at a time and refining the mapping coordinates of at least one product selected until a stop criterion is obtained.

18. The computer program product of claim 15, wherein a laboratory measure value is used as a feature for each building block in at least one variation site in the combinatorial library.

19. The computer program product of claim 15, wherein a computed value is used as a feature for each building block in at least one variation site in the combinatorial library.

20. The computer program product of claim 15, wherein at least some of the building block features represent reagents used to construct the combinatorial library.

21. The computer program product of claim 15, wherein at least some of the building block features represent chemical fragments of reagents used to construct the combinatorial library.

22. The computer program product of claim 15, wherein at least some of the building block features represent modified chemical fragments of reagents used to construct the combinatorial library.

23. The computer program product of claim 15, wherein the mapping function $f$ is encoded as a neural network.

24. The computer program product of claim 15, wherein the mapping function $f$ is a set of mapping functions $f_1$ through $f_n$, each encoded as a neural network.

25. A method for generating coordinates for products in a combinatorial library based on features of corresponding building blocks, the method comprising the steps of:
(1) obtaining mapping coordinates for a subset of products in the combinatorial library, wherein distances between the mapping coordinates represent similarity/dissimilarity relationships between the products;
(2) obtaining building block features for the subset of products in the combinatorial library;
(3) using a supervised machine learning approach to infer a mapping function $f$ that transforms the building block features for each product in the subset of products to a corresponding mapping coordinate for each building block feature of each product in the subset of products; and
(4) encoding the mapping function $f$ in a computer readable medium, whereby the mapping function $f$ is used to generate coordinates corresponding to additional products in the combinatorial library from building block features associated with the additional products.

* * * * *